US012635963B2

(12) United States Patent
Turner et al.

(10) Patent No.: US 12,635,963 B2
(45) Date of Patent: May 26, 2026

(54) THREE DIMENSIONAL X-RAY IMAGING SYSTEM

(71) Applicant: 3DIO, INC., Orem, UT (US)

(72) Inventors: D. Clark Turner, Mesquite, NV (US); Douglas P. Hansen, Spanish Fork, UT (US); Thomas L. Youd, Holladay, UT (US); Keith Decker, Pleasant Grove, UT (US)

(73) Assignee: 3DIO, Inc., Orem, UT (US)

( * ) Notice: Subject to any disclaimer, the term of this patent is extended or adjusted under 35 U.S.C. 154(b) by 833 days.

(21) Appl. No.: 17/658,004

(22) Filed: Apr. 5, 2022

(65) Prior Publication Data

US 2022/0225952 A1 Jul. 21, 2022

Related U.S. Application Data

(63) Continuation-in-part of application No. 16/610,203, filed as application No. PCT/US2018/030970 on May 3, 2018, now Pat. No. 11,432,781.

(Continued)

(51) Int. Cl.
*A61B 6/00* (2024.01)
*A61B 6/51* (2024.01)

(52) U.S. Cl.
CPC .............. *A61B 6/512* (2024.01); *A61B 6/486* (2013.01)

(58) Field of Classification Search
CPC ................................ A61B 6/025; A61B 6/512
See application file for complete search history.

(56) References Cited

U.S. PATENT DOCUMENTS 4,247,780 A 1/1981 Webber et al.
5,109,276 A 4/1992 Nudelman et al.
(Continued)

FOREIGN PATENT DOCUMENTS

CN 102858266 A 1/2013
CN 102860838 A 1/2013
(Continued)

OTHER PUBLICATIONS

Richard Webber: See sub-article, Three-Dimensional Image Display of Dental Structures https://pdfs.semanticscholar.org/083f/c4f9f814a60624d859b645b2750eca979858.pdf (Last accessed Mar. 2, 2020).

(Continued)

*Primary Examiner* — Dani Fox
(74) *Attorney, Agent, or Firm* — Kenneth E. Horton; Barnes & Thornburg LLP

(57) ABSTRACT

Three dimensional X-ray imaging systems are described in this application. In particular, this application describes a 3D dental intra-oral imaging (3DIO) system and associated methods using a series of 2D image projections. The methods include making a 3D image of an object by providing an X-ray source on a first side of a object to be imaged, positioning a substantially stationary X-ray detector on an opposite side of the object from the X-ray source, moving the X-ray source in a circular motion to multiple positions on the first side of the object, collecting multiple two dimensional (2D) images of the object in less than about 10 seconds when the X-ray source is located in the multiple positions, and reconstructing a three-dimensional (3D) image using the multiple 2D images. In some methods, 15 to 100 2D images of the object can be collected by pulsing the X-ray source for about 5 ms to about 40 ms per image in each of the multiple positions. In other methods, 15 to 100

(Continued)

2D images of the object can be collected in less than 10 seconds by pulsing the X-ray source for about 5 ms to about 40 ms per image in each of the multiple positions. These X-ray systems and methods offer a quick method of imaging an object, such as a tooth, while at the same time using a low radiation dose. Other embodiments are described.

20 Claims, 17 Drawing Sheets

Related U.S. Application Data

(60) Provisional application No. 62/500,914, filed on May 3, 2017.

(56) References Cited

U.S. PATENT DOCUMENTS

| | | | |
|---|---|---|---|
| 5,200,819 A | 4/1993 | Nudelman et al. |
| 5,200,838 A | 4/1993 | Nudelman et al. |
| 5,668,844 A | 9/1997 | Webber |
| 6,196,715 B1 | 3/2001 | Nambu et al. |
| 6,418,189 B1 | 7/2002 | Schafer |
| 6,549,607 B1 | 4/2003 | Webber |
| 6,801,597 B2 | 10/2004 | Webber |
| 6,810,278 B2 | 10/2004 | Webber et al. |
| 6,885,724 B2 | 4/2005 | Li et al. |
| 6,980,624 B2 | 12/2005 | Li et al. |
| 7,110,807 B2 | 9/2006 | Webber et al. |
| 7,751,528 B2 | 7/2010 | Zhou et al. |
| 7,801,587 B2 | 9/2010 | Webber et al. |
| 7,813,469 B2 | 10/2010 | Siltanen et al. |
| 8,126,112 B2 | 2/2012 | Massie et al. |
| 8,284,894 B2 | 10/2012 | Poorter |
| 9,036,776 B2 | 5/2015 | Sadakane et al. |
| 9,113,799 B2 | 8/2015 | Katsumata et al. |
| 9,144,406 B2 | 9/2015 | Dennerlein |
| 9,148,566 B2 | 9/2015 | Wagatsuma |
| 9,208,559 B1 | 12/2015 | Maschke |
| 9,351,701 B2 | 5/2016 | Yamakawa et al. |
| 9,408,579 B2 | 8/2016 | Yamakawa et al. |
| 9,427,286 B2 | 8/2016 | Siewerdsen et al. |
| 9,544,577 B2 | 1/2017 | Blassnig et al. |
| 9,629,590 B2 | 4/2017 | Katsumata et al. |
| 9,636,183 B2 | 5/2017 | Helm et al. |
| 9,668,705 B2 | 6/2017 | Yamakawa et al. |
| 9,700,740 B2 | 7/2017 | Maurer, Jr. |
| 9,713,505 B2 | 7/2017 | Helm et al. |
| 9,730,776 B2 | 8/2017 | Lal et al. |
| 9,743,893 B2 | 8/2017 | Inglese et al. |
| 9,782,136 B2 | 10/2017 | Zhou et al. |
| 9,795,348 B2 | 10/2017 | Ruijters |
| 9,855,013 B2 | 1/2018 | Morita et al. |
| 9,872,663 B2 | 1/2018 | Duewer |
| 9,888,893 B2 | 2/2018 | Hoernig |
| 9,898,840 B2 | 2/2018 | Klausz et al. |
| 9,901,309 B2 | 2/2018 | Defreitas et al. |
| 9,901,315 B2 | 2/2018 | Farbizio et al. |
| 9,907,516 B2 | 3/2018 | Litzenberger et al. |
| 9,907,520 B2 | 3/2018 | Zhou et al. |
| 10,039,508 B2 | 8/2018 | Abramovich et al. |
| 2003/0235265 A1 | 12/2003 | Clinthorne et al. |
| 2007/0133741 A1 | 6/2007 | Harding |
| 2012/0328071 A1 | 12/2012 | Katsumata et al. |
| 2014/0093032 A1 | 4/2014 | Dennerlein |
| 2015/0131774 A1 | 5/2015 | Maurer, Jr. et al. |
| 2015/0265237 A1 | 9/2015 | Keeve et al. |
| 2016/0220212 A1 | 8/2016 | Duewer |
| 2016/0317107 A1* | 11/2016 | Zhou .................... A61B 6/06 |
| 2017/0038484 A1 | 2/2017 | Cox |
| 2017/0281110 A1* | 10/2017 | Mandelkern ......... A61B 6/5264 |
| 2018/0146937 A1 | 5/2018 | Nariyuki et al. |

FOREIGN PATENT DOCUMENTS

| | | |
|---|---|---|
| CN | 101983034 B | 2/2013 |
| CN | 105411620 A | 3/2016 |
| CN | 106572826 A | 4/2017 |
| CN | 105873516 B | 7/2020 |
| DE | 3932151 A1 | 4/1991 |
| GB | 2533801 B | 9/2018 |
| JP | H10295680 A | 11/1998 |
| JP | 2005013738 A | 1/2005 |
| JP | 2006034451 A | 2/2006 |
| JP | 2015144898 A | 8/2015 |
| KR | 20120010639 A | 2/2012 |
| KR | 20140087207 A | 7/2014 |
| WO | 2017021520 A1 | 2/2017 |
| WO | 2017196413 A1 | 11/2017 |

OTHER PUBLICATIONS

Srinivasan Vedantham, PhD, Digital Breast Tomosynthesis: State of the Art https://pubs.rsna.org/doi/10.1148/radiol.2015141303 (Last accessed Mar. 2, 2020).

http://www.rsna.org/News.aspx?id=17933 (last accessed Mar. 2, 2020).

https://radiologykey.com/computed-tomography-7/ (Last accessed Mar. 2, 2020).

Yakimovsky and Cunningham entitled "A System for Extracting Three Dimensional Measurements from a Stereo Pair of TV Cameras", published in Computer Graphics and Image Processing 7, p. 195-210, 1978.

Guohua Cao, et al "A Stationary-Sources and Rotating-Detectors Computed Tomography Architecture for Higher Temporal Resolution and Lower Radiation Dose", EEE Access, Jan. 2014.

Abreu, M Jr et al. "Influence of the number of basis images and projection array on caries detection using tuned aperture computed tomography (TACT)." Dento maxillo facial radiology vol. 31,1 (2002): 24-31. doi:10.1038/sj/dmfr/4600656.

* cited by examiner

THREE DIMENSIONAL X-RAY IMAGING SYSTEM

CROSS-REFERENCE TO RELATED APPLICATIONS

This application is a continuation-in-part of U.S. application Ser. No. 16/610,203, filed on Nov. 1, 2019, which claims priority of PCT Application No. PCT/US2018/030,970, filed May 3, 2018, which claims priority of U.S. Provisional Application Ser. No. 62/500,914, filed May 3, 2017, the entire disclosures of which are incorporated herein by reference.

FIELD

This application relates generally to X-ray equipment, including X-ray devices and systems that are used for three dimensional imaging. More specifically, this application relates to an apparatus for obtaining intraoral X-ray images in a dental environment. The system generates a three dimensional (3D) reconstructed volume based on a plurality of two dimensional (2D) projection images. The 2D images are taken at different X-ray source positions located on a circle that defines the base of a regular geometric cone with the intraoral sensor located at the apex of the cone.

BACKGROUND

X-ray imaging systems typically contain an X-ray source and an X-ray detector. X-rays (or other types of radiation used for imaging) are emitted from the source and impinge on the X-ray detector to provide an X-ray image of the object or objects that are placed between the X-ray source and the detector. The X-ray detector is often an image intensifier or even a flat panel digital detector.

Intra-oral radiography is a standard imaging technique in dentistry, with bite-wing and periapical X-rays considered a standard of care in dental practice. However, there are many features of the tooth anatomy that are not visible in standard intra-oral radiographs as these are 2D projections of a 3D structure. Additionally, while bite-wing radiographs are very good at detecting interproximal caries, a slight variation in angle may serve to obscure the proper diagnosis due to overlapping with adjacent teeth or other factors. Tooth fractures and/or small cracks are not visible in radiographs unless the image projection angle is coincidentally aligned with the crack direction. For endodontics, curvature of the roots is not always visible because radiographs show only the projection and not the true length or vector of the root. In some cases, extra or accessory canals aren't visible if overlapped in the 2D image. Radiographs are also used for implant planning. While cone-beam computed tomography (CBCT) is often used for implant planning, the majority of implants are for a single tooth. Therefore, the patient receives a high relative dose by performing a CBCT scan of the entire oral cavity, when 3D image information is needed for only a single tooth.

SUMMARY

This application relates generally to three dimensional (3D) X-ray imaging systems. In particular, this application describes a 3D dental intra-oral imaging (3DIO) system and associated methods that use a series of 2D image projections. The methods include making a 3D image of an object by providing an X-ray source on a first side of a object to be imaged, positioning a substantially stationary X-ray detector on an opposite side of the object from the X-ray source, moving the X-ray source in a circular motion to multiple positions on the first side of the object, collecting multiple two dimensional (2D) images of the object in less than about 10 seconds when the X-ray source is located in the multiple positions, and reconstructing a three-dimensional (3D) image using the multiple 2D images. In some methods, 15 to 100 2D images of the object can be collected by pulsing the X-ray source for about 5 ms to about 40 ms per image in each of the multiple positions. In other methods, 15 to 100 2D images of the object can be collected in less than 10 seconds by pulsing the X-ray source for about 5 ms to about 40 ms per image in each of the multiple positions. These X-ray systems and methods offer a quick method of imaging an object, such as a tooth, while at the same time using a low radiation dose.

BRIEF DESCRIPTION OF THE DRAWINGS

The following description can be better understood in light of the Figures which show various embodiments and configurations of the imaging systems.

Figure 1:
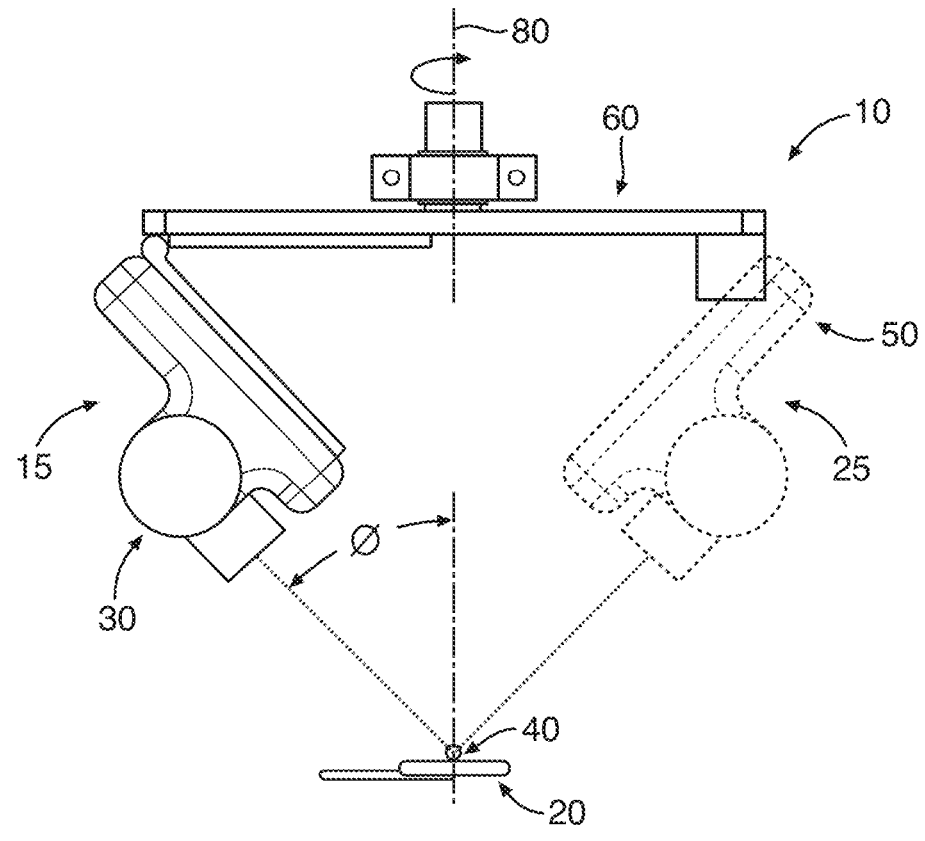
FIG. 1 shows a view of some embodiments of a 3DIO imaging system.
Figure 2:
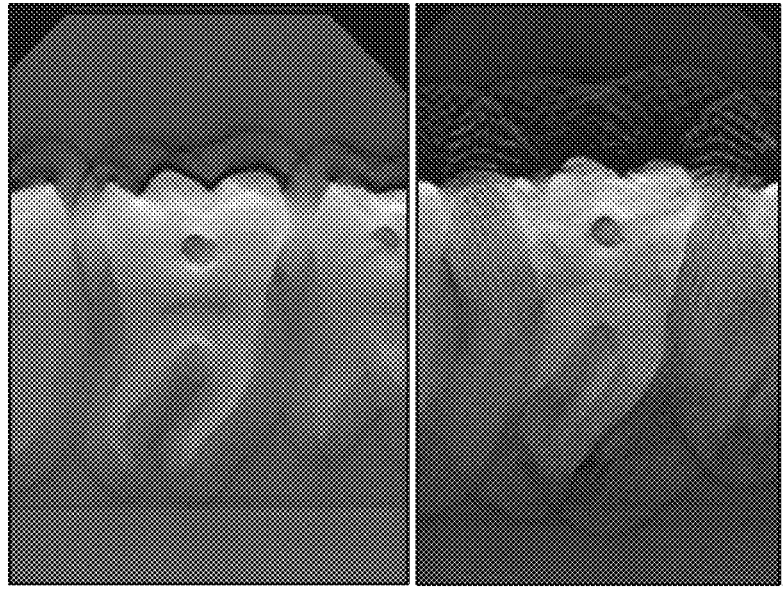
FIG. 2 shows another view of some embodiments of images produced by a 3DIO imaging system with sample 3D slices at a plane chosen to demonstrate high contrast between the simulated carie and the surrounding tooth. The left image is taken at a 15-degree cone angle and the right images at a 30-degree cone angle. The image defects due to z-plane artifacts can be seen in the right image.

Together with the following description, the Figures demonstrate and explain the principles of the structures and methods described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray systems can be implemented and used without employing these specific details. Indeed, the described systems and methods can be placed into practice by modifying the described systems and methods and can be used in conjunction with any other apparatus and techniques conventionally used in the industry. For example, while the description below focuses on imaging systems for dental imaging, they can be used for other purposes such as medical imaging, veterinary imaging, industrial inspection applications, and anywhere where X-ray radiography equipment is currently being used to generate a standard 2D X-ray image.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Dental X-ray radiography can be performed by positioning an X-ray source on one side of an object (e. g., a tooth or a set of teeth) and causing the X-ray source to emit X-rays through the teeth and toward an X-ray detector located on the other side of the teeth, either inside or outside of the mouth. As the X-rays pass through the teeth, jaws, and other tissues, their energies are absorbed to varying degrees depending on the tissue composition. The X-rays arriving at the X-ray detector form a 2D X-ray image based on the cumulative absorption through the teeth, bones and other mouth structures. The intraoral X-ray images provide a high level of detail of the tooth, bone, and supporting tissues. They also allow dentists to find cavities, examine tooth roots, evaluate the condition of the bony area around the tooth, determine if periodontal disease is present or a concern, and monitor the status of developing teeth, among other things. Increasing the applied X-ray dose typically increases the number of X-ray photons contributing to the image. Given that X-ray images are typically dominated by Poisson noise, the signal-to-noise ratio (SNR) improves as additional X-ray dose is applied. A minimum X-ray dose is therefore typically required to successfully visualize a given feature of clinical interest. Beyond that necessary minimum dosage, increasing dosage does not necessarily result in significant additional clinical utility.

Intraoral radiography is the primary method of dental imaging since it provides relatively high resolution, and limited field of view images for most routine dental needs. But current 2D radiographs of objects (such as a tooth of a patient) are often ambiguous for detection of problems or defects because they are not usually able to visualize fractures in a tooth, and because they use plane projections, they can miss tooth curvature and other anomalies important to dental diagnosis and treatment. Despite the many technological advances, the radiographic diagnostic accuracy for some of the most common dental conditions has not improved in many years and, in some cases, remains low. Examples include caries detection, root fracture detection, and assessment of periodontal bone loss. In addition, as a two dimensional (2D) imaging modality, the technique suffers from superposition of overlying and underlying structures and loss of spatial information in the depth or Z-axis dimension.

Panoramic imaging, a popular form of extraoral imaging, visualizes the entire maxilla, mandible, temporomandibular joints (TMJ) and associated structures in a single image, but it is subject to considerable geometric distortion and has relatively low spatial resolution compared with intraoral radiography. Again, this technique is limited because of the 2D representation of a 3D object. The 2D image results in superposition of overlying structures and loss of spatial information in the depth dimension. Consequently, important dimensional relationships are obscured, observed sharpness is reduced, objects of interest are lost, and pathology contrast is reduced.

Accordingly, 3D imaging can be used in some dental procedures. Tomosynthesis is one type of 3D imaging that provides 3D information about a patient reconstructed from X-ray images of the patient taken from multiple perspectives within a scan angle much smaller than the 360° or at least 180° of computed tomography (CT) or cone-beam computed tomography (CBCT), with typical angular ranges covering a range from a minimum of perhaps 10° to perhaps an upper limit of 60° or 70°. Digital tomosynthesis improves the visibility of anatomical structures by reducing visual clutter from underlying and overlying normal anatomy. Some examples of current clinical tomosynthesis applications include chest, abdominal, musculoskeletal, and female breast imaging.

A variation of the tomosynthesis technique, called Tuned Aperture Computed Tomography (TACT), was investigated in the late 1990s for dental imaging. TACT significantly improved the diagnostic accuracy for a number of tasks compared to conventional radiography. These improvements included root fracture detection, detection and quantification of periodontal bone loss, implant site assessment, and the evaluation of impacted third molars. The results for caries, however, were inconclusive. TACT was not adopted clinically because the technology was not practical for patient imaging. To acquire the multiple projection images, an X-ray source was mechanically moved around the patient. A fiduciary marker was used to determine the imaging geometry. The process was time consuming (e.g., approximately 30 minutes per scan) and required high operator skill to successfully accomplish image acquisition. The difficulty of precisely determining the imaging geometry parameters and long imaging acquisition time due to mechanical motion of the source makes TACT impractical.

On the other hand, CBCT as a three-dimensional (3D) imaging modality has found wide acceptance in dentistry. It is especially useful in surgical planning procedures such as dental implant and orthodontic treatment planning, and evaluation of endodontic and pathological conditions. There are, however, several disadvantages associated with CBCT in comparison to 2D radiography, among them being much higher system cost, excess noise and artifacts from metal dental restorations/appliances, which reduce image quality; significantly lower resolution of CBCT compared to 2D; the limitation that CBCT cannot be performed with the patient in the operatory chair; acquisition, reconstruction, and interpretation time are greatly increased relative to 2D radiography, thereby reducing clinical efficiency; and significantly higher ionizing radiation doses, which increase the radiation burden for the patient.

Still, cone-beam computed tomography (CBCT) is becoming widely used in dentistry as a supplement to 2D radiographs. In CBCT, a patient's head is positioned in-between a large imaging detector and an opposing X-ray source. The detector and source rotate around the head while taking multiple 2D images. Using these 2D images, a 3D image of the patient's oral and maxillofacial anatomy can be reconstructed. This technique works very well for imaging the entire oral cavity and displaying the spatial relationships between the teeth and other bony structures located in the head of a patient. The CBCT technique is, therefore, often used for dental implants and orthodontic procedures where such spatial relationships are important.

However, projecting X-rays through the entire head, as required in CBCT procedures, leads to high X-ray scattering and attenuation from non-resolving anatomy. This can result in spatial resolution in the CBCT image that is much worse than intra-oral radiography using 2D radiographs with an intra-oral sensor positioned right next to the tooth of interest. In addition, the patient radiation dose in CBCT procedures is considerably higher than in intra-oral 2D radiography. CBCT procedures are not often used to image a single tooth, or just a few teeth, due to the high radiation dose. Thus, CBCT is not an effective and safe imaging tool for the majority of dental procedures which only involve a single tooth or a few adjacent teeth.

CBCT does not provide significant improvement for caries detection. Caries is the most common dental disease. The World Health Organization estimates that 60-90% of school children and nearly all adults have dental caries at some point in time. If carious lesions are detected early enough, (e.g., before cavitation), they can be arrested and re-mineralized by non-surgical means. When carious lesions go undetected, they can evolve into more serious conditions that may require large-scale restorations, endodontic treatment, and, in some cases, extractions.

The detection sensitivity of caries has not seen any significant improvement in the past several decades. 2D intraoral radiography is the current gold standard, with a reported sensitivity ranging from 40% to 70% for lesions into dentine and from 30% to 40% for lesions confined to enamel. 3D imaging with CBCT simply does not provide sufficient spatial resolution to enable a significant improvement for caries detection.

Vertical root fractures (VRF) are also not well detected by CBCT. Detecting vertical root fractures (VRF) represents a clinically significant diagnostic task with important ramifications in tooth management. VRFs are considered one of the most frustrating tooth conditions associated with endodontic therapy. Overall detection of VRFs remains poor. The ability of CBCT to detect initial small root fractures is limited by its relatively low resolution. Furthermore, excess beam hardening, streak artifact, and noise result in both significantly decreased sensitivity and increased false positive root fracture diagnosis.

To overcome some of these limitations, the systems and methods described herein provide a diagnostic imaging system with high resolution, 3D capabilities, reduced metal artifact sensitivity, and lower radiation burden to patients than CBCT. As well, the systems and methods described herein provide an intra-oral tomosynthesis system for 3D dental imaging that can rapidly obtain 3D dental images with the X and Y spatial resolution of conventional 2D intraoral dental radiography and significantly better Z resolution than CBCT 3D imaging. Indeed, the systems described herein use intra-oral imaging techniques that can be presented as a high resolution 3D image. These 3DIO (three dimensional, intra-oral) systems provide a simple 3D imaging technique that provides a 3D high resolution image using 2D radiographs taken at a low radiation dose.

Some embodiments of a 3DIO system are illustrated in FIGS. 1-12. FIG. 1 shows the geometry of the 3DIO system with a rotation scheme shown with the X-ray source at position 15 and position 25 around axis of rotation 80. In FIG. 1, the 3DIO system 10 comprises an imaging detector 20 that is located inside the mouth (not shown). The imaging detector 20 can be substantially stationary adjacent to the tooth (or teeth) 40 of a patient, or even completely stationary relative to the tooth using any stabilizing mechanism such as a bite block or other sensor holder device. The 3DIO system 10 also contains an X-ray source 30 that is optionally located within a housing 50. The housing 50 can be connected to a support arm 60.

The 3DIO system 10 can contain any X-ray source 30 and X-ray detector 20 that allows the system 10 to take multiple 2D X-ray images or radiographs. The X-ray source 30 can contain any source that generates and emits X-rays, including a standard stationary anode X-ray source, micro-focus X-ray source, rotating anode X-ray source, and/or a carbon nano-tube or micromachined (Spindt cathode) X-ray source. In some embodiments, the X-ray source can operate with about 40 to about 90 kV and from about 1 to about 10 mA. In other embodiments, the X-ray source can operate with about 55 kV to about 75 kV and between about 3 mA and about 9 mA. In still other embodiments, the X-ray source can operate with about 60 kV to about 70 kV and between about 4 mA and about 7 mA. In some embodiments, the X-ray source and X-ray detector can be made modular so that different sizes and types of X-ray sources and X-ray detectors can be used.

The X-ray detector 20 can contain any detector that detects X-rays, including an image intensifier, CCD array, CMOS/scintillator array, and/or a digital flat panel detector. In some configurations, the detector can have a substantially square shape with a length on one side ranging from about 2.5 cm to about 6 cm. In other configurations, though, the X-ray detector 20 does not need to have a substantially square shape but can have a rectangular shape to roughly match the size of a tooth of a patient.

In some configurations, the X-ray detector 20 can be synchronized with the X-ray source 30. Thus, the X-ray detector can be activated substantially at the same time that the X-ray source is activated, thereby capturing a 2D-projection image generated by the X-ray radiation passing through the patient's tooth/teeth and onto the detector.

In some configurations, the X-ray detector 20 can have quick readout speed. In the 3DIO systems described herein, this read-out speed can range from about 5 to about 40 frames per second. This quick speed allows the necessary number of frames to be taken in a reasonable period of time. In other embodiments, the detector read out speed can be more than about 7 frames per second. In yet other embodiments, the detector read out speed can be more than about 12 frames per second. In still yet other embodiments, the detector read out speed can range from about 5 to about 15 frames per second. In even other embodiments, the read out speed can range between any combination or sub-combination of these amounts.

In some embodiments, the number of pixels in the X-ray detector needs to be limited to a reasonable number, such as within the range of about 1,500,000 to about 4,750,000 pixels, with a more advantageous number of pixels ranging from about 2,000,000 to about 3,250,000 pixels More pixels not only increase the image read-out time, but also add more complexity to the reconstruction algorithm used to render the 3D image from the 2D images. The number of pixels in the detector should also be kept within this range because of the detector size constraints imposed by the need to fit into the patient's mouth, the reduction in sensitivity that accompanies a reduction in pixel size, matching the detector resolution to the resolution capabilities of the X-ray source for best X-ray optical performance, as well as reducing the complexity of the math required to reconstruct the image. Consequently, in these embodiments only 2 to 3 teeth can be adequately imaged in most cases because of the size of the detector that can fit within the patient's mouth.

Figure 9:
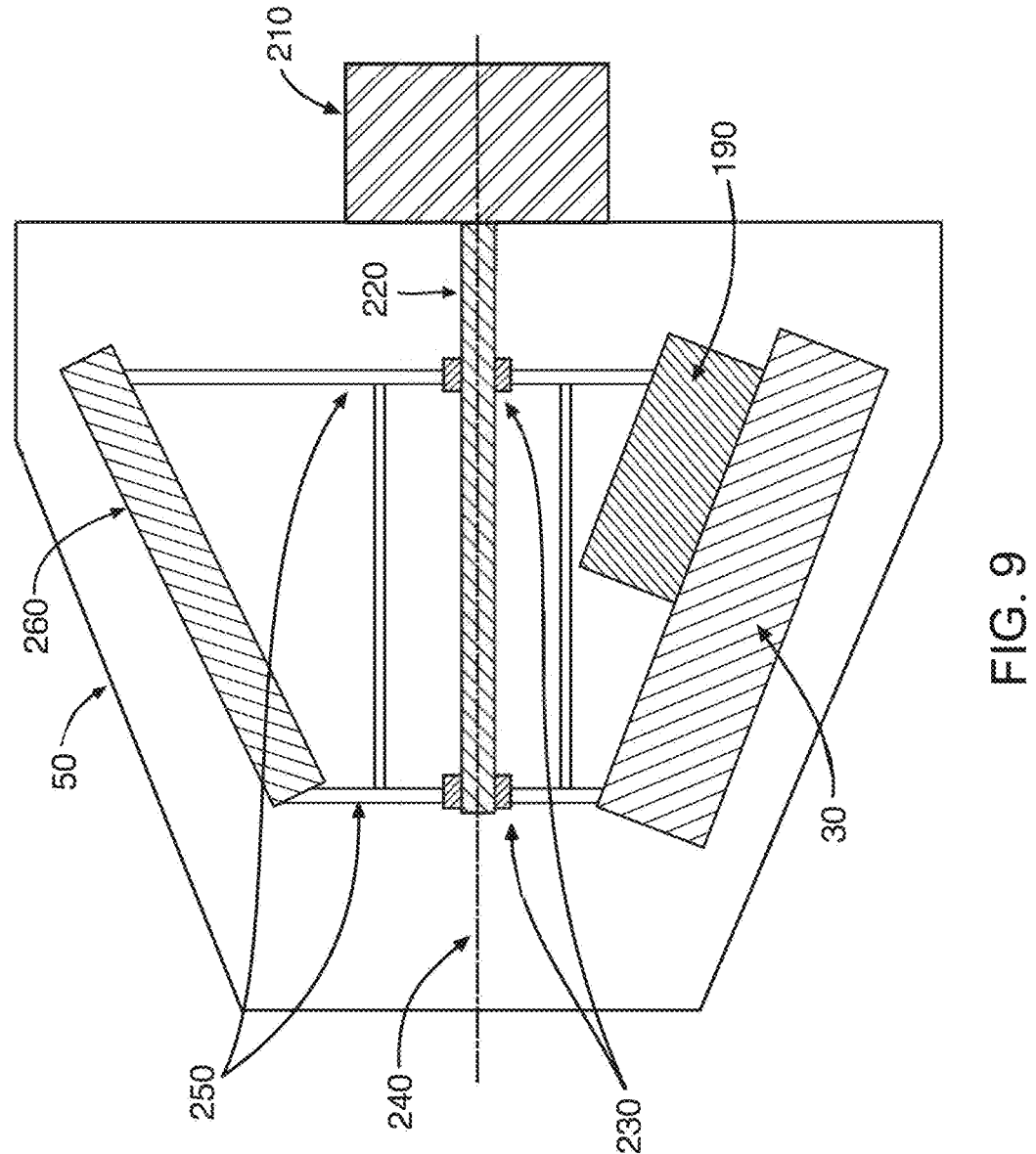
FIG. 9 shows some embodiments of the housing and components contained in the housing of a 3DIO imaging system.

As shown in detail in FIG. 9, the X-ray source 30 can optionally be contained in housing 50. The housing 50 can be configured with a first part enclosing the X-ray source 30 as shown in FIG. 9. The housing 50 also encloses a second part that contains a counterweight 260 for the X-ray source 30, power electronics 190, and other components, which facilitates smooth vibration-free rotary motion of the source 30. The X-ray source 30 and its associated power electronics 190 and the counterweight 260 are located as necessary on rotating mechanical assembly 250 which supports the X-ray source 30, the power electronics 190, counterweight 260, and other components (not shown) to properly balance the rotating mechanical assembly 250. The rotating mechanical assembly 250 is mounted to axle 220 (or other mechanical device to support the mechanical assembly) with an axis of rotation 240 using the bearings and/or electric motor assembly 230 to enable drive rotation of the mechanical assemble 250.

As shown in FIG. 9, the housing 50 can be configured so that it is a single part that encloses both the X-ray source 30 and these components. In other configurations, the housing can be separated into different parts to contain the X-ray source 30 and other components. As shown in FIG. 9, the electronic components for control and power conditioning 210 can be located just outside of the housing 50. In other embodiments, these electronic components 210 can be located on the support arm or other convenient location. In yet other embodiments, these electronic components 210 can be located internal to the housing 50.

Figure 10:
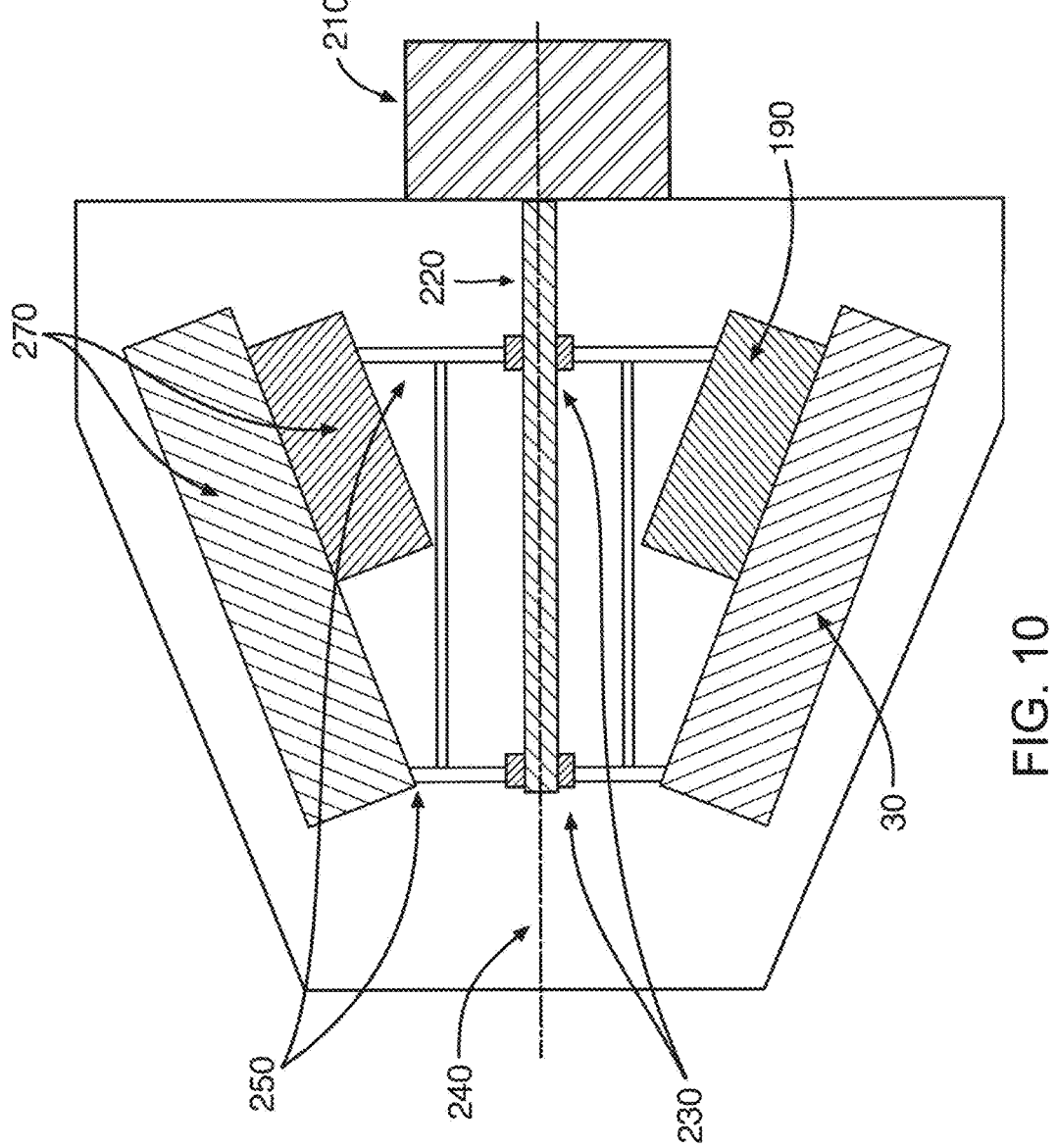
FIG. 10 illustrates some embodiments of using multiple X-ray sources in the housing a 3DIO imaging system.
Figures 11A, 11B:
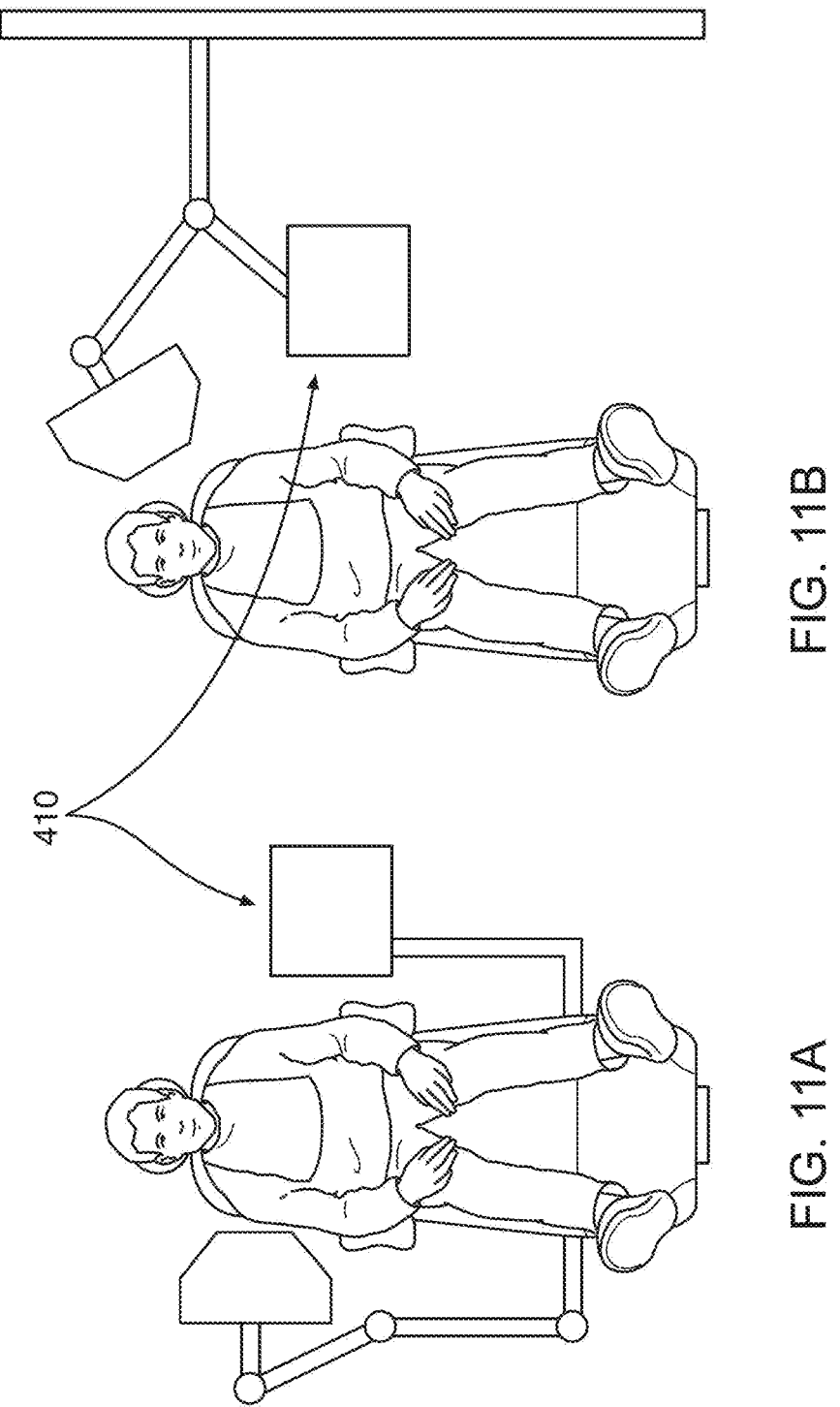
FIGS. 11A and 11B depict yet other embodiments of the 3DIO imaging systems.

In some embodiments, multiple X-ray sources can be used in the 3DIO systems. In these embodiments, as shown in FIG. 10, multiple X-ray sources (30, 270) would enable a reduction in the mechanical rotation speed required to cover all of the desired source positions needed to generate the 3D image. These sources could be fired in an alternating manner or otherwise as required to obtain all of the desired 2D images from the various X-ray source locations within the head. The remainder of the components in FIG. 10 can be similar to those shown in FIG. 9, with the exception that the second X-ray source and its associated high voltage electronics 270 have replaced the counterweight 260.

The use of multiple X-ray sources 30 within the housing 50 would also provide the benefit of reduced motion blur in the X-ray images obtained since the X-ray source is moving at a lower velocity than would be required with a single source. The use of multiple, substantially-identical sources 30 would also negate the requirement for a counterweight since the multiple sources can be positioned to result in a balanced rotational system. More than two X-ray sources could be incorporated into the 3DIO system, with the full 360 degrees of the circle being divided by the number of sources used so that the multiple sources are distributed evenly around the circular frame on which they are mounted. Of course, the use of multiple sources will increase the system over-all cost and complexity, so the needs and constraints of the intended use will need to be considered in choosing the number of sources to be included within a particular 3DIO system.

Figure 12:
FIG. 12 depicts some embodiments of a non-linear array of multiple X-ray sources that can be used in the 3DIO imaging system.
Figure 12:

Some conventional X-ray systems contain multiple X-ray sources that are arranged in a linear array and are operated without moving the linear array. In some embodiments of the 3DIO system using multiple X-ray sources, the sources can be arranged in a two-dimensional array. In these embodiments, the two-dimensional array of multiple x-way sources could be configured with a rectangular, square, pseudo-random, hexagonal, or circular array. The array could have any number of sources that does not unduly increase the cost while still providing the desired functionality described herein, such as 3, 4, 5, 6, 7, 8, 9, 10, 12, and 16 sources, or even more. The number of X-ray sources could be balanced against how much rotation is needed for multiple X-ray sources to take the desired number of images. In some configurations, 3, 4, 5, or even 6 X-ray sources are used in a substantially circular array as shown in FIG. 12. The X-ray sources 20 are positioned roughly equidistance about the center "A" of the circle. The circular array can be rotated in a circular motion so that images taken in the array substantially cover 360 degrees. For example, if 4 X-ray sources are used and are separated 90 degrees from each other, the circular array only needs to rotate about 90 degrees to cover the full 360 degrees of the circle.

In some configurations, the 3DIO systems can contain a removable power source (such as a battery) and optionally a power supply. In these configurations, the power source and the power supply can be located on or in any supporting structure which the 3DIO systems might be used with. For example, the supporting electronics for the power source and the power supply, as well as the supporting electronics for the image display and for the wireless data upload described herein, can also be located internal or external to a support structure to which the housing 50 is connected, such as stand 300 shown in FIG. 8. Thus, in these configurations, the system 10 does not require an external power cord. Incorporating the power source (i.e., the battery), the power supply, and the supporting electronics all in or on the external structure allows the 3DIO systems to be portable and moved from one dental station to another. With such a configuration, the power source can easily be replaced or swapped. Of course, if needed, the 3DIO system 10 can be configured so that it is alternately, or additionally, powered using external power from a power cord that is plugged into a wall outlet. In other configurations, multiple power supplies can be provided for the source, detector, and control electronics.

The support arm 60 can have any configuration that allows the X-ray source 30 in the housing to direct X-ray beams at the desired angle through the tooth (or teeth) and on the detector 20. In the embodiments shown in FIG. 1, the support arm 60 has a substantially straight configuration with the housing 50 connected to an end thereof. In other configurations, the support arm need not be straight and can have jointed or articulated sections. In yet other configurations, the housing 50 can be connected to the support arm 60 at any location other than the end.

In other embodiments, the 3DIO system 10 also contains a frame that can be connected to the support arm 60. The frame can be configured to give a number of easy gripping options for a user during operation of the 3DIO system 10. The frame can contain one or more cross members, one or more length members, and one or more handles. The length and diameter of the various members in the frame can be changed as needed for a variety of operators. In some embodiments, the frame can be configured as a modular unit so different cross members (or length members or handles) can be used to replace the existing cross members (or length member or handles). Thus, the frame provides the ability for a user (or operator) to grip and position the 3DIO system 10 prior to operation, if desired.

The frame can also contain buttons (or triggers) that can be used to operate the 3DIO system 10. In some configurations, the 3DIO system 10 can be configured with two or more triggers. In these configurations, the triggers can be provided in multiple locations on the frame so that regardless of how the 3DIO system 10 is held in the hands of an operator, a trigger is always convenient for the operator to use. For example, the triggers can be placed on the cross members, the length members, and/or the handles. In another example, the trigger can be connected by a long cable to the rest of the 3DIO system, thereby enabling a remote triggering process. These multiple triggers make it easier to operate and easier to hold in the hand of the user when it is used to acquire images of a patient. For the triggers to operate the device, the needed internal electronics can be carried inside the frame. In other configurations, one or more of these triggers can be a remote trigger connected by a wired or wireless control. Optional button shrouds and/or compulsory push sequences can be used to prevent accidental X-ray emissions.

Figure 8:
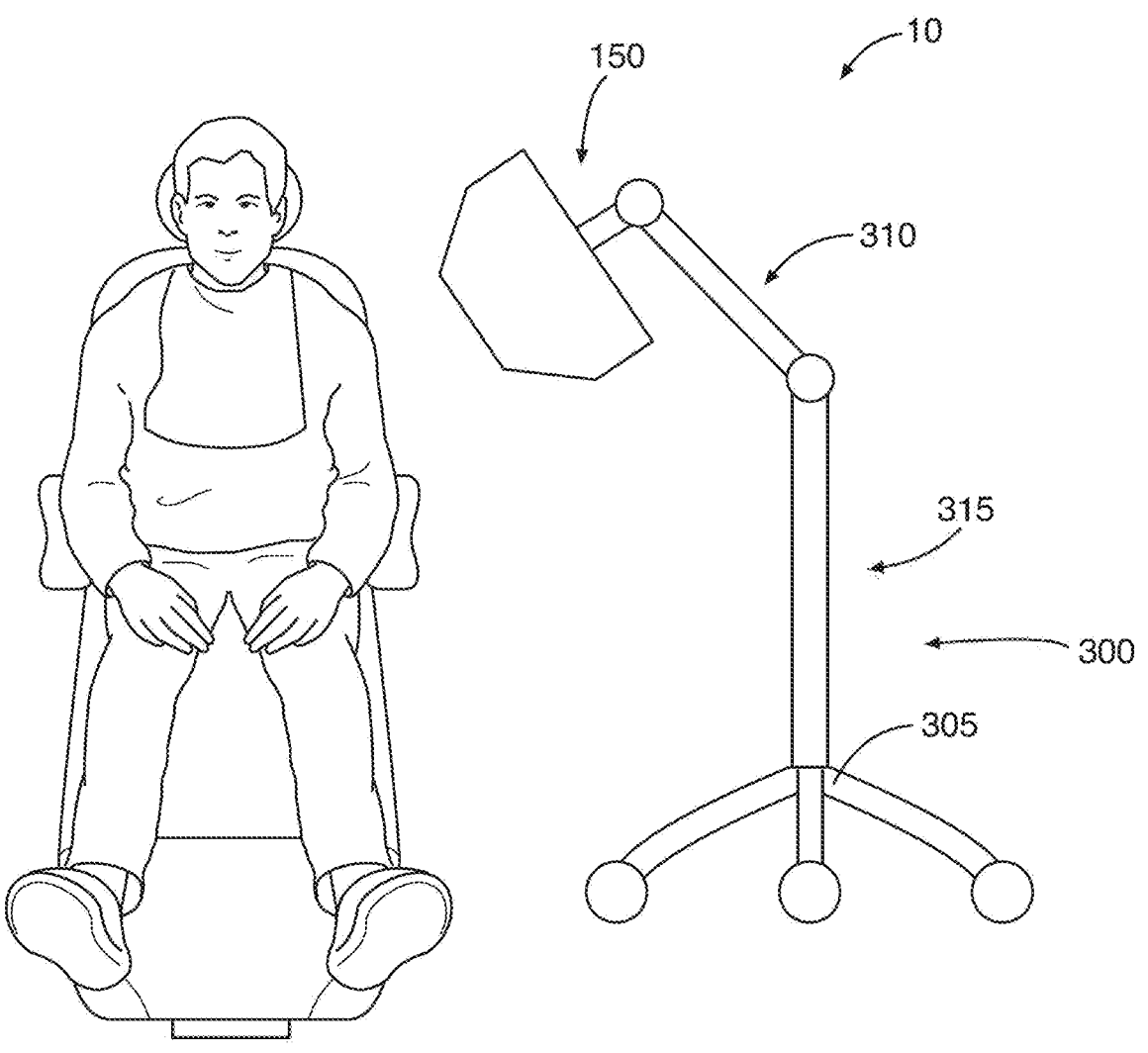

Another example of an external support structure is illustrated in FIG. 8. In this Figure, the 3DIO system 10 with a frame 150 can be connected to a stand 300. The stand 300 contains a base 305 and an arm 315 extending upwards towards an extension 310. The extension 310 is connected to the joint which is, in turn, connected to the frame 150 of the 3DIO system 10. In other configurations, the 3DIO system 10 can be connected to a movable support structure. In such configurations, the movable support structure can be configured to move across a floor while supporting the 3DIO system 10. Thus, the movable support structure can comprise one or more wheels, shelves, handles, monitors, computers, stabilizing members, limbs, legs, struts, cables, and/or weights (to prevent the weight of the imaging arm and/or any other component from tipping the movable support structure). Thus, the movable support structure could comprise a wheeled structure connected to a stand that contains the joint that is connected to the frame 150 of the 3DIO system 10.

Figure 7B:
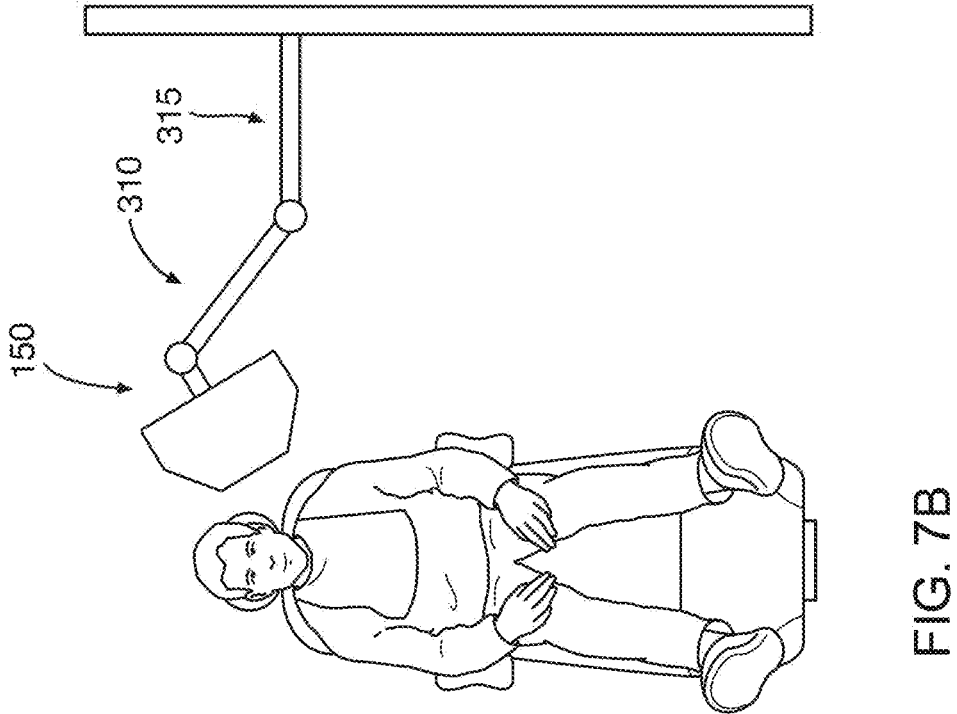
FIGS. 7A, 7B, and 8 show some embodiments of a 3DIO imaging system mounted to equipment in a dental office.
Figure 7A:
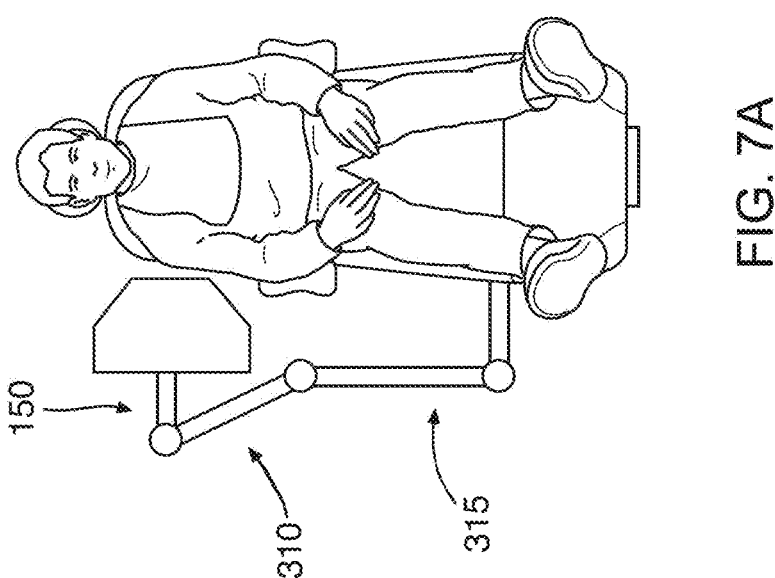

In some configurations, the 3DIO system can be removably or permanently mounted to any wall or any chair, as depicted in FIGS. 7A and 7B. The 3DIO system can be configured with any size, shape, and weight that will allow it to be mounted to a wall or chair, as shown in FIGS. 7A and 7B. The 3DIO system can also be configured with any size, shape, and weight so that it can be removably or permanently mounted to any desired support stand, as shown in FIG. 8. In one example, the 3DIO system can have a head volume of about 36 cm×about 36 cm×about 34 cm and a head weight of about 10 Kg. In another example, the 3DIO system can have a head volume of about 27 cm×about 27 cm×about 25 cm and a head weight of about 6 Kg. Of course, the head volume or head weight could have any amounts between these two examples.

The volume and weight of the 3DIO should be minimized as much as possible for ease of use and ease of alignment. To reduce the size and/or weight, the 3DIO system can be equipped with small and light-weight components. Over the last decade, there have been significant innovations in miniaturization of X-ray tubes. These light-weight sources can greatly simplify the task of motion automation for the 3DIO systems described herein. In addition, newer CMOS detectors are much more sensitive, resulting in less dose to the patient than required with conventional CCD designs. The new CMOS detectors also have very high read-out speeds allowing for rapid collection and transmission of multiple 2D images. To achieve the 3DIO systems described herein, the X-ray source (or X-ray tube) should fit within a volume of about 13 cm×about 7 cm×about 8 cm and weigh less than about 1.9 Kg. As well, CMOS detectors with capability of at least 5 (or more) frames per second should be used. One way to achieve X-ray sources that meet these requirements would be to use a carbon-nanotube or spindt-cathode (micromachined silicon or similar technology) electron source within the X-ray source as this technology will simplify the X-ray tube design, enabling a smaller X-ray source.

In some configurations, the 3DIO system 10 can comprise any suitable locking mechanism that can quickly lock and unlock the movement of the support arm 60 or the housing 50. For instance, the locking mechanism can comprise a motorized lock, an electric lock, a radio controlled lock, or cable actuated locks, etc.

The 3DIO system can also be configured to be integrated with any dental station. Thus, the 3DIO system can be configured to connect with, or be moved to, a first dental station and operated to take images of a first patient. Then, the 3DIO system can be removed from the first dental station and then connected with a second (or third, fourth, etc.) dental station to take images of additional patients.

Figure 4:
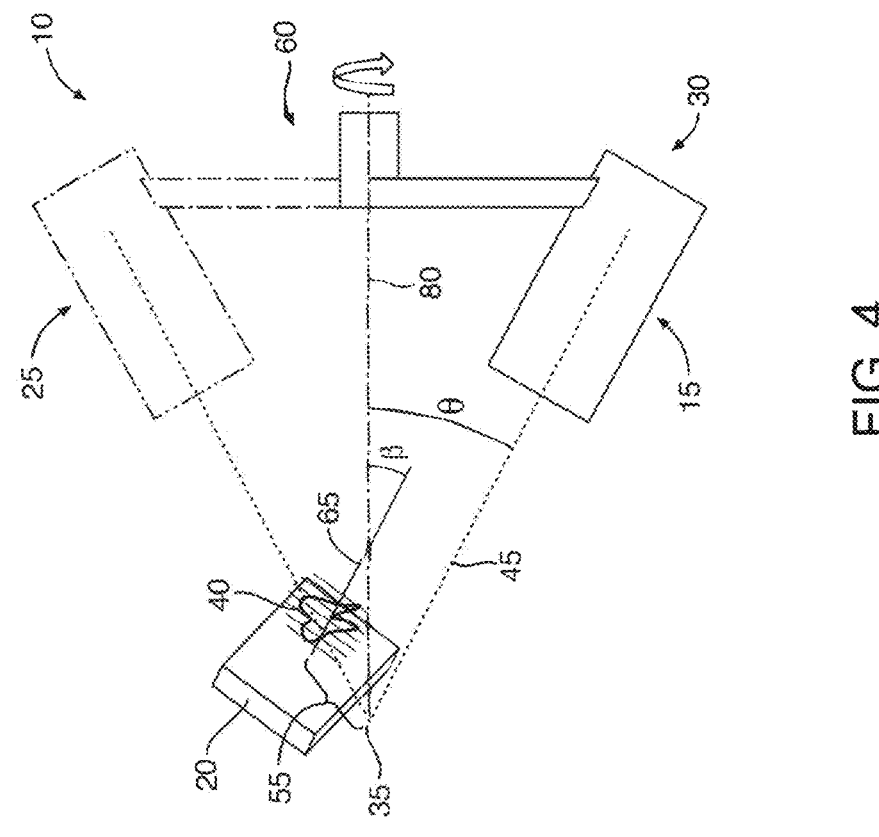
FIGS. 3-4 show some embodiments of the geometry of some components in a 3DIO imaging system.
Figure 3:
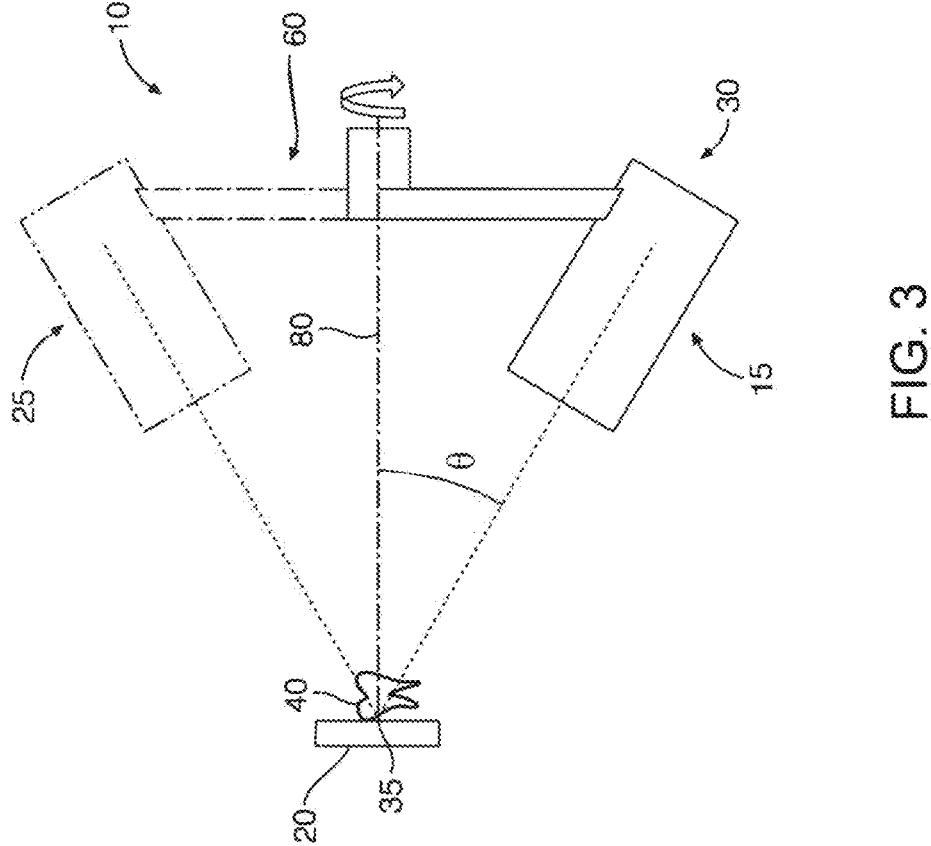

As depicted in FIGS. 3-4, the 3DIO system can also contain a geometric calibration mechanism. In some configurations, the calibration mechanism uses tooth features as fiducial markers. In other configurations, a geometric calibration could use the image data for calibration as opposed to fiducial markers. FIG. 3 shows an ideal geometry of the 3DIO system 10 with the detector 20 substantially parallel to the tooth 40 and substantially perpendicular to the axis of rotation 80 of the X-ray source 30 from position 15 to position 25. The X-ray beam 45 from the X-ray source 30 impinges on the tooth 40 at an angle θ from the axis of rotation 80 with the axis of rotation located on the center of rotation 35 which is also centered on the detector 20. FIG. 4 shows a real-world example where the alignment of the X-ray source 30 is not perfect with respect to either the tooth 40 or the detector 20. In FIG. 4, the center of rotation 35 is not centered on the detector 20 but is offset by a distance 55. The axis 65 (that is normal to the detector 20) is aligned at an angle β from the axis of rotation 80. In FIG. 4, the alignment of the rotation axis 80 and the location of the center of rotation 35 with respect to the tooth 40 and the detector 20 must be determined using calibration techniques.

In some embodiments, the mechanical motion of the X-ray source can be partially or fully automated so that little to no operator intervention is required. The motion that is automated would be a constant velocity rotation in most embodiments, as this is the simplest operational mode. Other embodiments, however, could use a stop-start approach in which the X-ray source is held stationary during each X-ray exposure and then quickly moved or rotated to the next position. Still other embodiments could use an operational mode in which different rotational velocities are used at different points in the rotation. As well, the rotation velocity, or the stop-start motion, could be synchronized with the operation of the X-ray source and the detector so that the X-ray source and panel are properly triggered or operated when the X-ray source is at the desired position in its movement or path.

This rotary automation can be accomplished by mounting a light-weight X-ray source(s) on a motion gantry that could be optionally enclosed in a single housing. As noted herein, the housing could be mounted on a wall-mount arm like modern intra-oral X-ray sources, but there would be no motion of the housing itself. The partially or fully automated system will allow the operator to collect 3D images with a technique that is simple for the operator to activate so that the operator and the patient experience are comparable to the experience and technique of conventional single 2D radiographs. Ideally, the entire imaging sequence could be activated by pushing a single button or issuing a single command to a computer control system.

Using the partial or full automation of the movement of the X-ray source allows the 3DIO systems to operate on a substantially-continuous or even in some configurations a continuous basis. The X-ray source may pause only long enough to provide the desired amount of X-rays before moving again, or it may be allowed to move continually. In most configurations, the X-ray source need only pause for about 5 ms to about 40 ms milliseconds while sending the X-ray beams toward the object (i.e., tooth). In other configurations, the X-ray source need only pause about 10 ms to about 30 ms milliseconds while sending the X-ray beams toward the object. In other configurations, the X-ray source need only pause about 20 milliseconds while sending the X-ray beams toward the tooth. Then, it only takes about 10 ms to about 100 ms milliseconds to re-position the X-ray source (optionally within the housing 50) before sending another set of X-ray beams. While the X-ray source is moving to another location, the computer system can download the first image from the detector to prepare the detector for the next image in the sequence. The time required to download the image from the detector may require from about 10 milliseconds to over 100 milliseconds, depending on the characteristics of the detector and the computer system. This download time can be simultaneous with the X-ray system motion, but the detector should be ready to acquire a new image before the X-rays can be sent towards the detector again. The X-ray source can be moved and re-positioned, and the image downloaded, as many times as needed. In other words, the imaging process on average can range from about 15 ms to about 140 ms per image taken.

In other configurations, the imaging process can range from about 30 ms to about 45 ms per image taken.

The length of the X-ray pulse from the X-ray source balances several constraints so that it can take the desired number of images within the desired time frame to arrive at the required image quality. As described herein, a higher X-ray brightness improves the image quality by reducing the noise in the image since more photons are produced by the X-ray source. But a higher brightness (and more photons) requires a higher tube current which will increase the power requirements of—and heat generated in—the X-ray source, leading to a larger head size and weight. And while more photons can also be achieved by a longer pulse time, since the number of photons is a factor of the time of the pulse, if the X-ray pulse is too long, the time required to take the necessary multiple 2D images will increase, leading to increased challenges with patient motion and patient comfort. The length of the X-ray pulse can also affected by how fast the detector can process the X-ray image formed by passing the X-rays through the object. In some embodiments, the X-ray source can be pulsed at full power for about 5 ms to about 40 ms per image. In other embodiments, the X-ray source can be pulsed for about 10 ms to about 30 ms per image.

The timing and sequencing of the X-ray exposures required to generate the 2D image data that will be processed into a 3D image needs to be as quick as possible. It is desirable that the entire imaging process be completed within a period of from about 1 seconds to about 10 seconds, about 2 to about 7 seconds, or even about 3 to about 5 seconds, with shorter times being preferred for reasons of patient comfort and because a short time makes it easier for the patient to remain motionless during the imaging process. For example, if the imaging sequence needs to be complete within 6 (or 7) seconds and a total of 24 (or 28) images are needed within that 6 seconds, the 3DIO system will take 4 images per second. The X-ray source within the housing would need to complete nearly one complete rotation during those 6 seconds, or have a rotational speed of approximately 10 rpm. Since the X-ray source can be pulsed in this example at full power for about 10 ms to about 40 ms per image, it leaves approximately 230 ms to 240 ms available for the X-ray detector to read out the image data and prepare to receive the next X-ray pulse, which would occur every 250 ms at a different position of the X-ray source and thus generate the next 2D image. Thus, the entire imaging process for a tooth can be completed quickly (i.e., less than about 3 to about 5 seconds and even about 1 or about 2 seconds) so that motion of the patient does not affect the imaging process, or a simple patient stabilization device (i.e., a chin rest) is sufficient to control patient motion. In another example, if the imaging sequence needs to be complete within 3 seconds and a total of 30 images are needed within that 3 seconds, the 3DIO system could take 10 images per second. The time for the X-ray pulse and the rotation speed would be adjusted accordingly relative to the previous example. Thus, the rotational speed would be about 20 rpm, the X-ray source would need to pulse at about 7 ms up to about 35 ms, and the system would acquire 10 images per second or an image every 120 ms, with a faster image acquisition time helpful. In other configurations, it can possible to reduce the image acquisition time (meaning the time from the initiation of the X-ray pulse to the completion of image readout by the sensor) to as low as about 70 milliseconds. This would enable the imaging systems to function at up to about 15 frames per second acquisition rate, with a corresponding rotational speed of 30 rpm, or an increase in the number of frames up to about 45 images.

If needed to image another tooth, the optional housing 50 and detector located within the patient's mouth can then be moved to another position relative to the patient's teeth. After the detector and optional housing have been repositioned, the imaging of the additional tooth can proceed in similar manner as described above. This process can be repeated to image as many teeth as desired.

Using the 3DIO systems described herein allows the operator to drastically reduce the time needed to take the multiple 2D images and use them to render the 3D image. Typically, the process for rendering the 3D images using the multiple 2D images can take less than about 120 seconds. In other embodiments, this time can range from about 30 seconds to about 90 seconds. Given the time needed to take the 2D radiographic images described above, the complete process for taking the 2D images and creating the 3D images can range from about 10 seconds to as long as 140 seconds, depending on the processing power available to process the acquired 2D images into the 3D image. In other embodiments, the complete process for taking the 2D images and creating the 3D images can range from about 30 seconds to about 100 seconds. In even other embodiments, the complete process for taking the 2D images and creating the 3D images can range from about 10 seconds to about 45 seconds.

As described, the 3DIO system can create a 3D image by capturing a first 2D radiographic image of the tooth or teeth at a first angle, moving the position of the X-ray source to take another image from a different angle, and then using a reconstruction algorithm to render a 3D image from the two 2D radiographic images. In many configurations, more than two 2D radiographic images will be used to create the 3D images. In some embodiments, the number of 2D radiographic images can range anywhere from 3 to over 1000 images. In other embodiments, the number of 2D radiographic images can range anywhere from 6 to over 40 images. In yet other embodiments, the number of 2D radiographic images can range anywhere from 15 to 32 images. The actual number of images that are used will vary for the configuration of the imaging system, depending on the desired image acquisition time and the resolution and quality required in the 3D image. The more 2D radiographic images that are used, the better the resolution and quality of the 3D image but the longer the imaging procedure will take, the higher the radiation dose to the patient, and the more time will be required for the 3D image calculations. On the other hand, the fewer 2D radiographic images that are used, the lower the resolution and quality of the 3D image but the quicker the imaging process can be.

Figure 5:
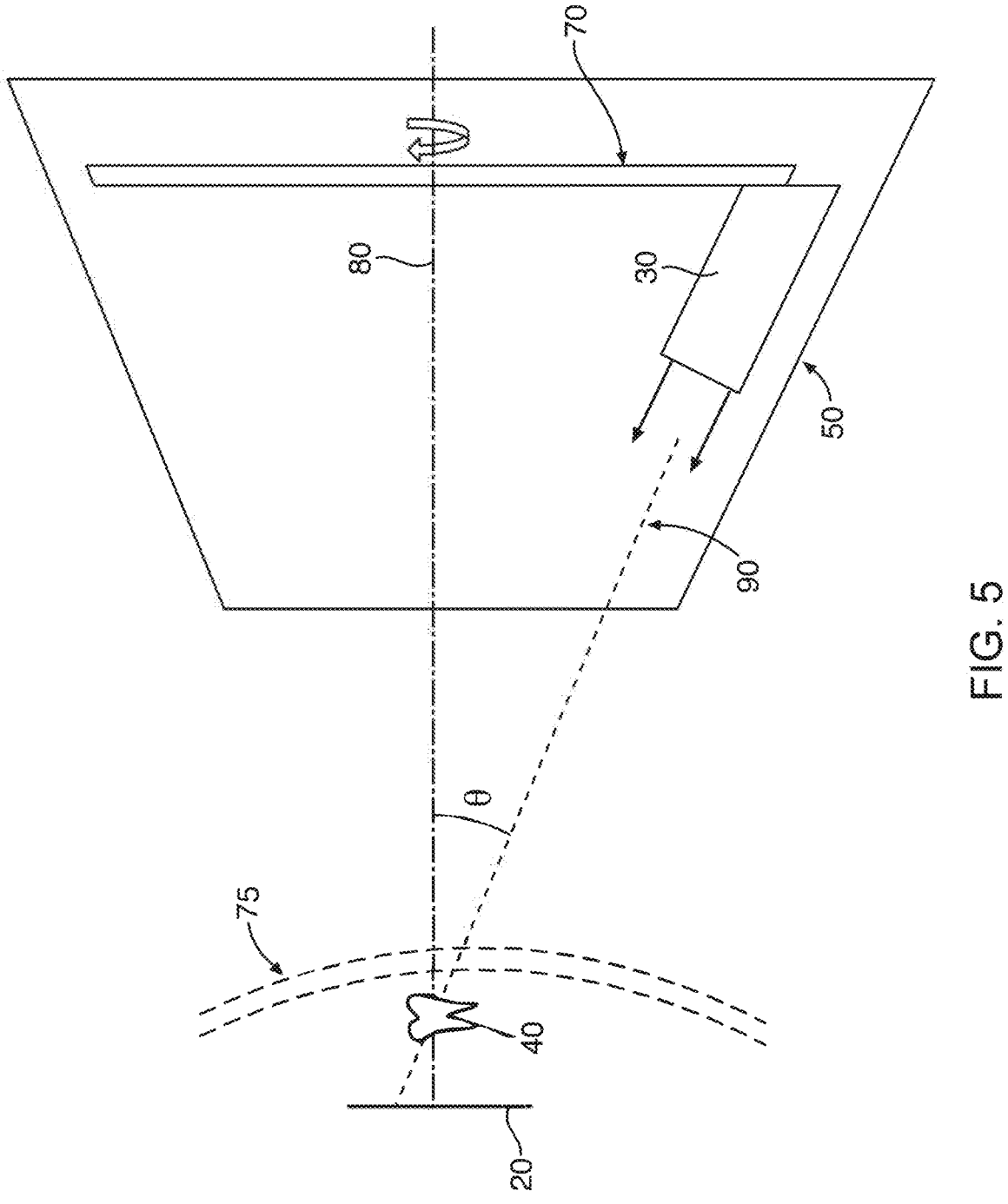
FIGS. 5-6 show some embodiments of the movement of the X-ray source in a 3DIO imaging system.
Figure 6:
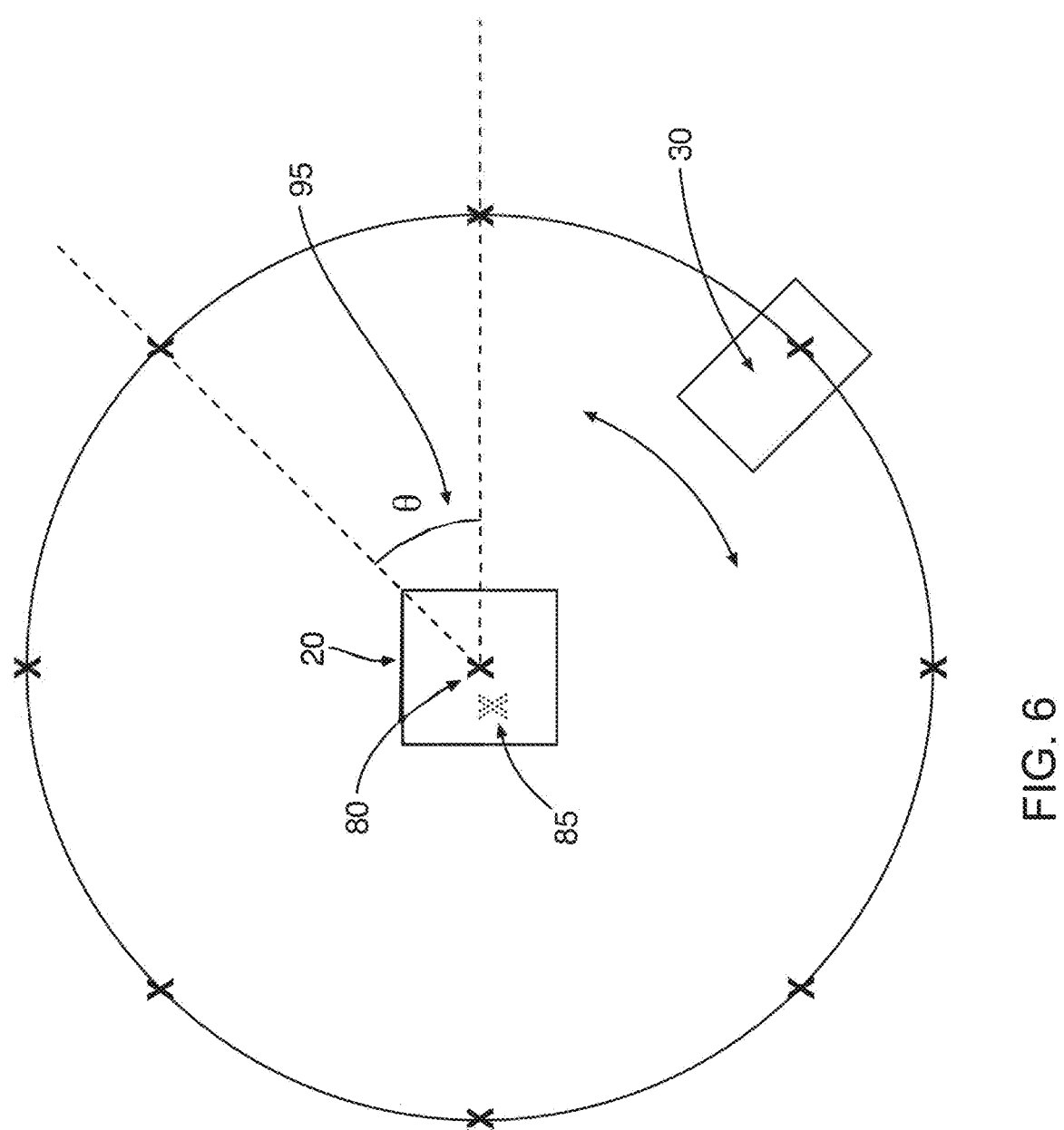

The X-ray source can be moved (or rotated) in a substantially circular motion in a plane substantially parallel to the detector 20 located behind a patient's cheek 75, as shown in FIGS. 5-6. The angle θ shown in FIG. 5 can range from any value near 0 degrees to near 90 degrees depending on what angle will provide the best 3D image quality, with angles between approximately 10 degrees and about 35 degrees producing good images. In some configurations, the angle can range from about 15 to about 23 degrees. In other configurations, the angle can range between any combination or sub-combination of these amounts.

The angle θ of the cone formed by the rotating X-ray source and the X-ray detector impacts the distance between the object and detector, or depth, of the region of interest that can be imaged in three dimensions. For a given angle, if the object to be imaged (i.e., tooth) is too far away from the sensor, an entire image may not be captured. FIG. 16 shows that the tooth is not fully imaged because the X-rays beams (illustrated as coming from the left) impinging on the detector do not pass through the portion of the tooth 42 desired to be imaged. This relationship between the angle θ and the imaging depth (how far from the sensor an object can be and still be fully imaged) creates a trade-off or optimization situation. For the angle θ and a given imaging depth, the optimum combination can be determined by the desired image resolution and quality, and the maximum imaging depth required for the application. It is well known in the mathematics of 3D reconstruction that the image resolution and quality will be improved with a larger angle θ, all other factors being held equal. As shown in FIGS. 13-16, however, the imaging depth, or the maximum distance from the sensor that can be imaged in all of the 2D images and thus fully reconstructed in the 3D reconstruction, will be reduced as the angle θ is increased. Thus, in some configurations, there is a maximum angle that is practical in the dental imaging application because the tooth/teeth to be imaged must be some distance from the sensor. In some dental configurations, though, the maximum practical angle that still provides a useful imaging depth is about 35 degrees.

Figures 13, 14:
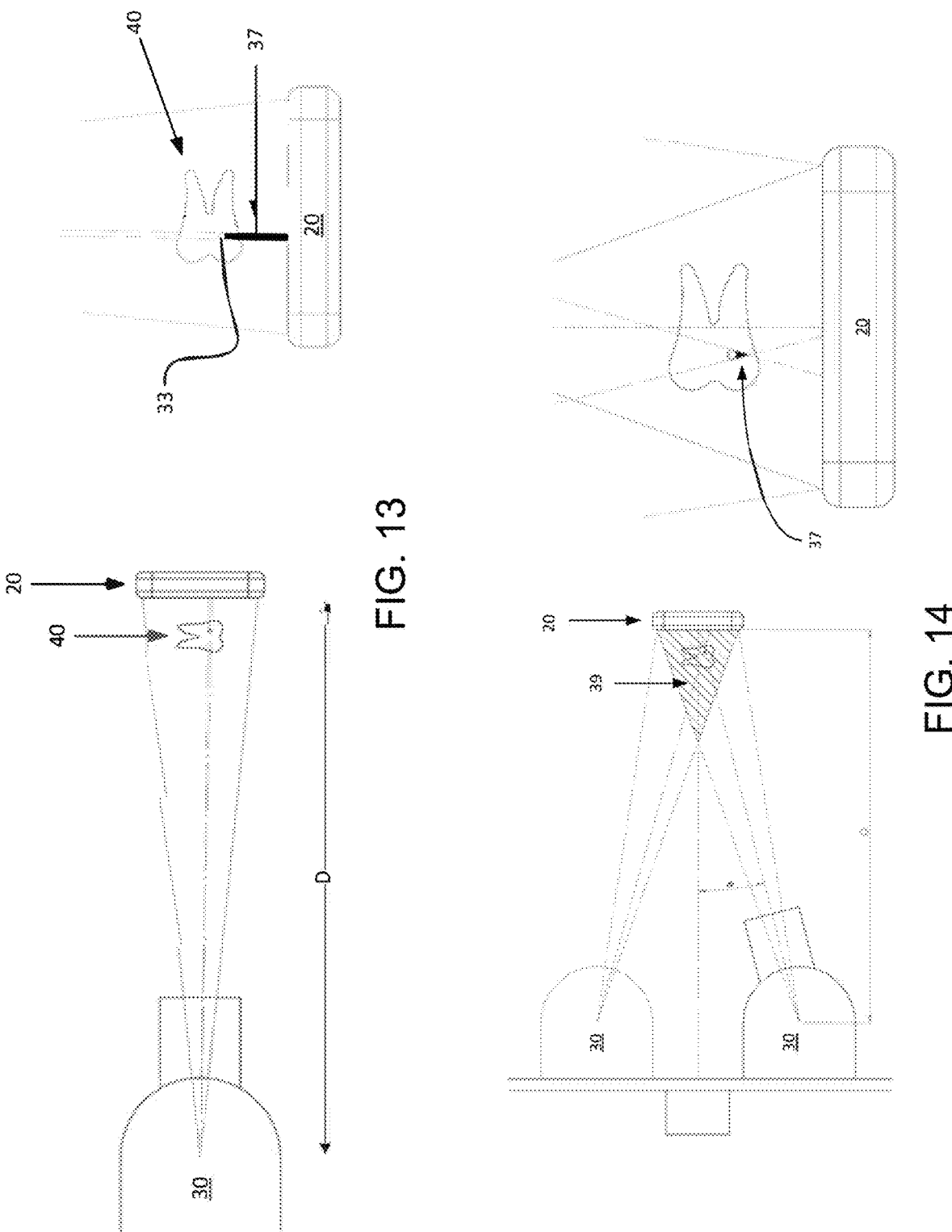
FIG. 13 shows some embodiments of the effect of an X-ray opaque object in a tooth on the normal-incidence X-ray image.
FIG. 14 shows how images taken at various angles fills in the detail that is missing in the normal-incidence image of the embodiments shown in FIG. 13.

FIGS. 13-16 also illustrate why there also exists a minimum practical angle in some configurations of the 3DIO systems. FIGS. 13-16 illustrate the relationship between the incident angle θ and what portion of the tooth 40 is imaged as the angle θ is changed. As shown in FIG. 13, the X-ray beams emitted from the X-ray source 30 are used to image tooth 40 that is located near the X-ray detector 20. The tooth 40 contains a cavity with a filling 33. The material of the filling 33 often absorbs the X-ray beams impinging on the tooth 40, creating an opaque object within the tooth 40. FIG. 13 depicts the situation when the angle θ is zero in which case the imaging depth can be essentially infinite but there is no 3D image information obtained. In FIG. 13, it can also be seen that an opaque object 33 within the tooth (a metallic filling or any other object that would essentially block all X-rays) creates what could be considered to be a "hole" in the X-ray image. This hole or region of missing detail 37 occurs because all of the tooth detail in line with the opaque object 33 both before and after the opaque object 33 is lost because no X-ray signal from this region reaches the detector. In FIG. 14, where the angle θ is increase to about 14 degrees, it can be seen that the region of missing detail 37 that is completely obscured by the opaque object 33 (in FIG. 13) is significantly reduced because the X-rays from the left and right side (and all of the other X-ray exposures at angles that are not depicted) effectively "see" the detail in front of and behind the object (region 37) that was obscured in the normal-incidence situation shown in FIG. 13.

Figure 15:
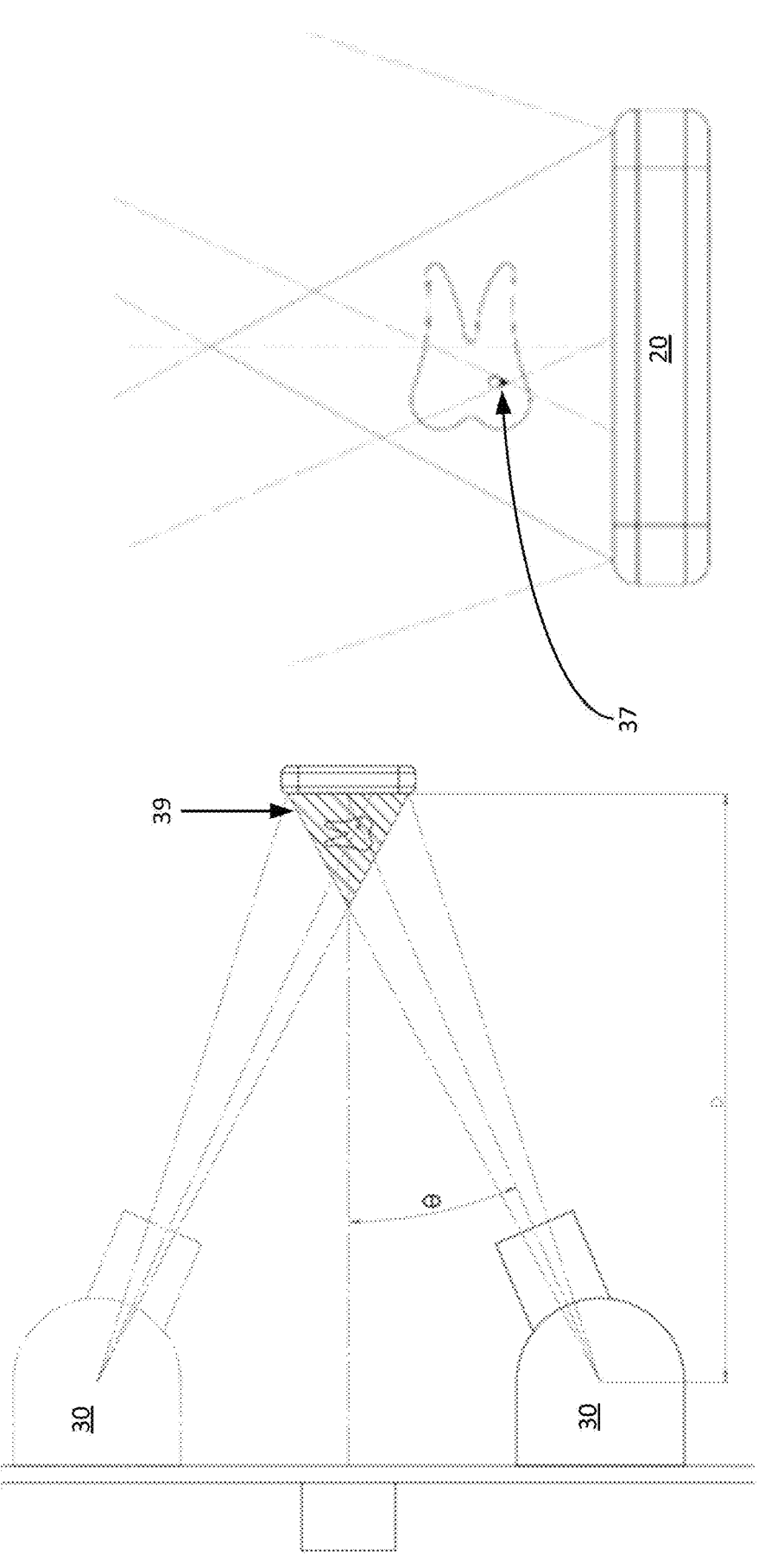
FIG. 15 shows how larger angles fill in more missing details in the normal-incidence image of the embodiments shown in FIG. 13.
Figure 16:
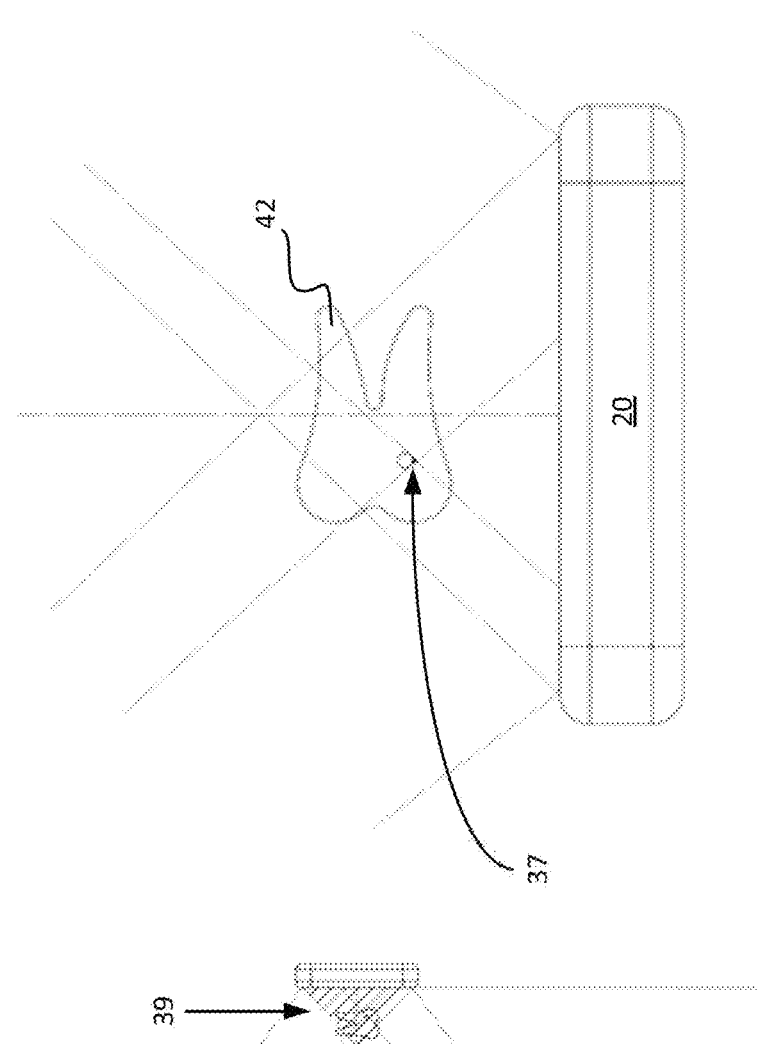
FIG. 16 shows how angles that are too large reduce the depth of field of the X-ray image because parts of the tooth are not captured in the various X-ray images.
Figure 16:
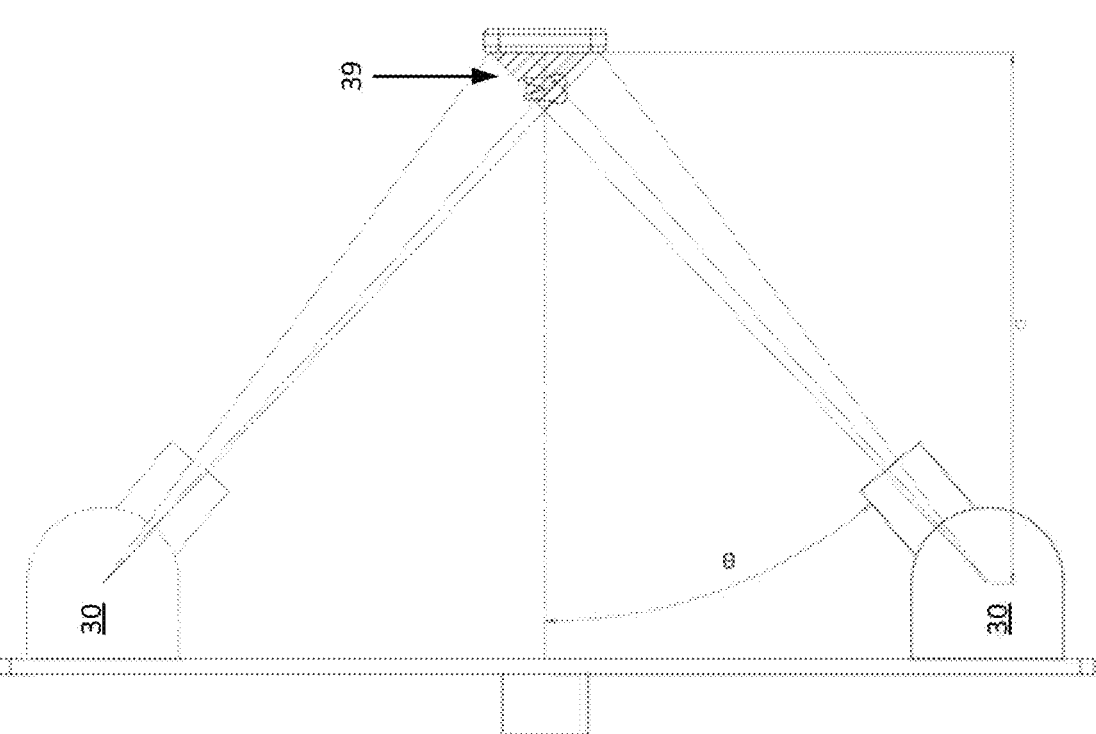

FIG. 15 depicts a larger angle θ of about 23 degrees and shows that the region of missing detail 37 is again reduced in size when compared to FIG. 14. FIG. 16 depicts an even larger angle θ of about 40 degrees and a further reduction in the size of the region of missing detail 37. Of course, as discussed herein, the tooth in FIG. 16 is not completely imaged. So further increasing the angle θ to improve one aspect of the image quality eventually reaches a point where other factors begin to reduce the over-all image quality, which is why the angle θ typically range from about 10 degrees to about 35 degrees in some configurations of the 3DIO systems.

FIG. 14 also shows that increasing the angle θ provides a better image of the tooth 40. In this Figure, the angle θ has been increased to about 14 degrees. A broader angle θ creates a reconstruction zone 39 where the X-ray beams have a different field of view because of the increased angle θ. As can be seen in FIG. 14, the blind spot 37 behind the tooth in FIG. 14 is smaller than the blind spot 37 in FIG. 13. FIG. 15 illustrates that when the angle θ is increased even more (i.e., to about 23 degrees), the blind spot 37 is decreased even more. But the larger angle θ in FIG. 15 also creates a smaller and shorter reconstruction zone 39 since the apex of the reconstruction zone 39 is closer to the detector 20. FIG. 16 illustrates that when the angle θ is increased even more (i.e., to about 40 degrees), the blind spot 37 is decreased even more, almost disappearing. Again, the larger angle θ in FIG. 16 creates a smaller and shorter reconstruction zone 39 since the apex of the reconstruction zone 39 is closer to the detector 20 than that shown in FIG. 15. Indeed, in FIG. 16 the reconstruction zone 39 creates a field of view that does not image part of the tooth 42. Thus, the 3DIO system uses an angle θ that, for a given image depth, is able to capture a full image of the tooth while at the same time reducing any blind spot behind the tooth in the image.

Figure 17:
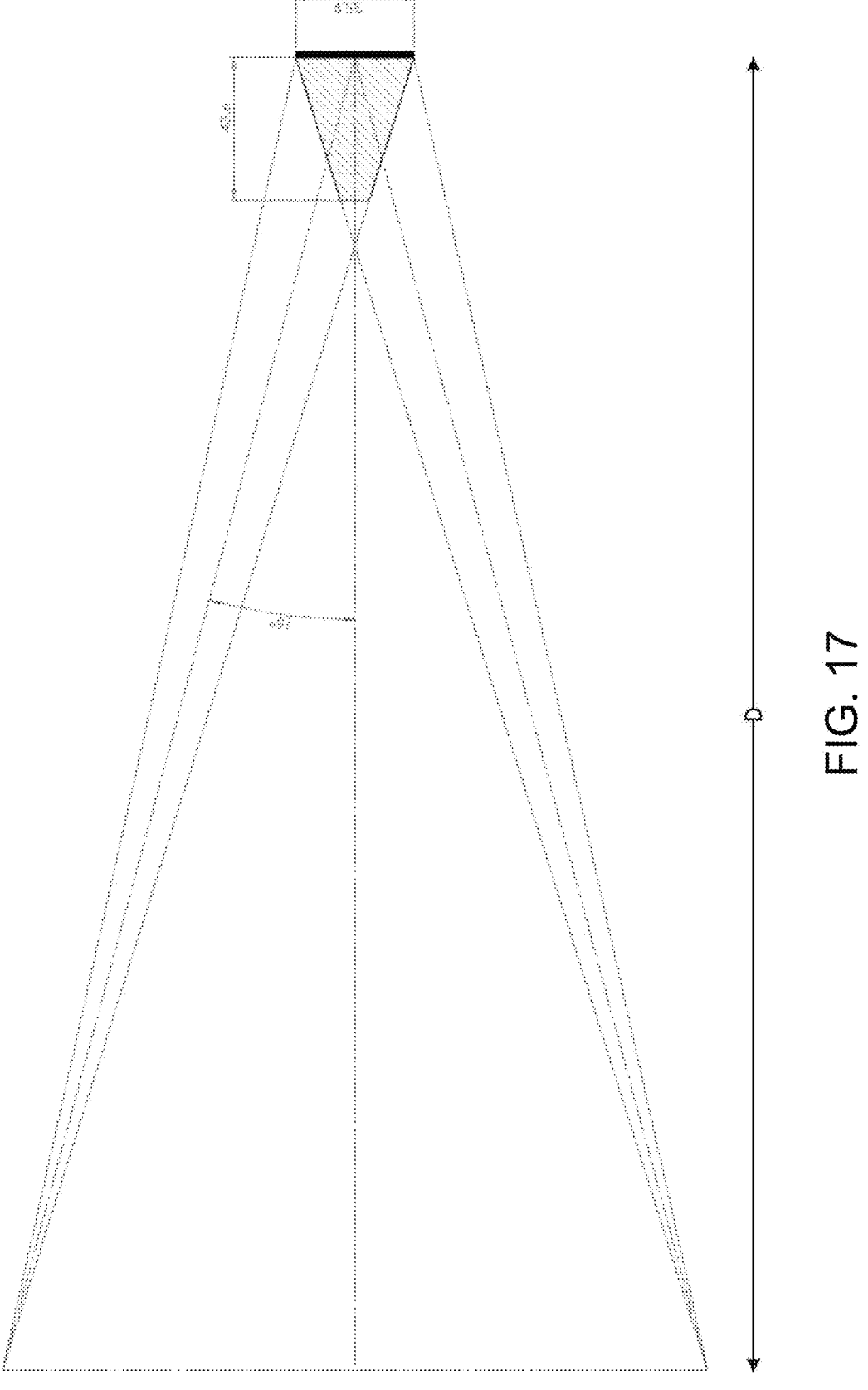
FIG. 17 illustrates the reconstruction zone in the 3DIO system when the cone angle between the X-ray source and detector is about 15 degrees.
Figure 18:
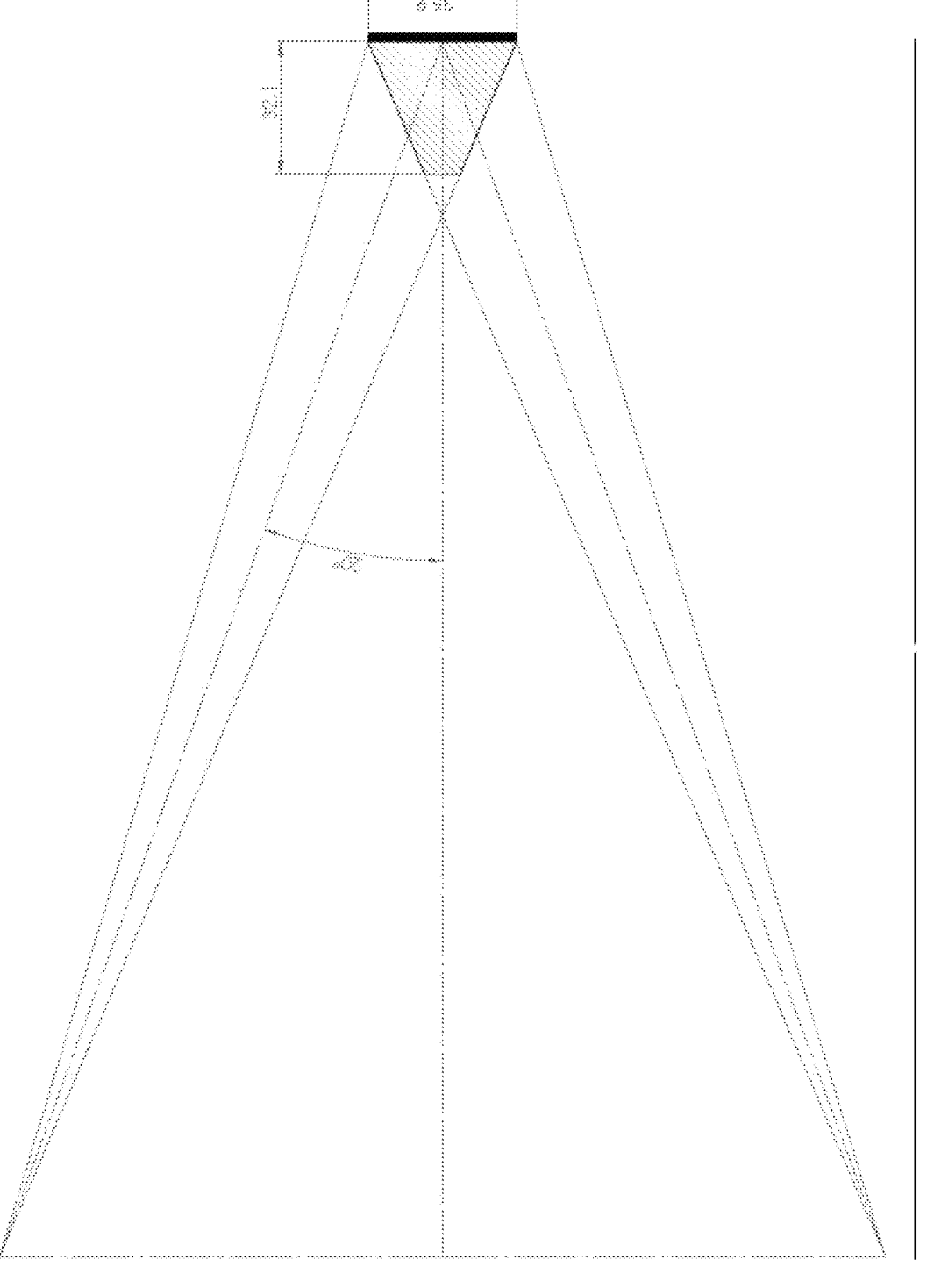
FIG. 18 illustrates the reconstruction zone in the 3DIO system when the cone angle between the X-ray source and detector is about 20 degrees.
Figure 19A:
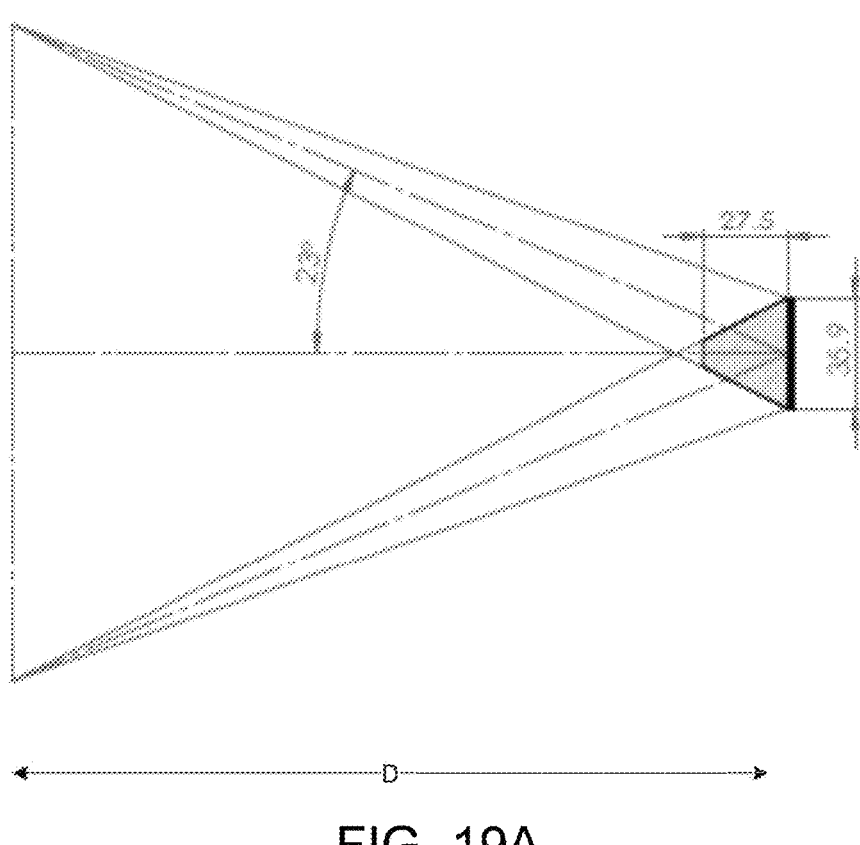
FIGS. 19A and 19B illustrate the reconstruction zone in the 3DIO system when the cone angle between the X-ray source and detector is about 23 degrees for two different sizes of detector.
Figure 19B:
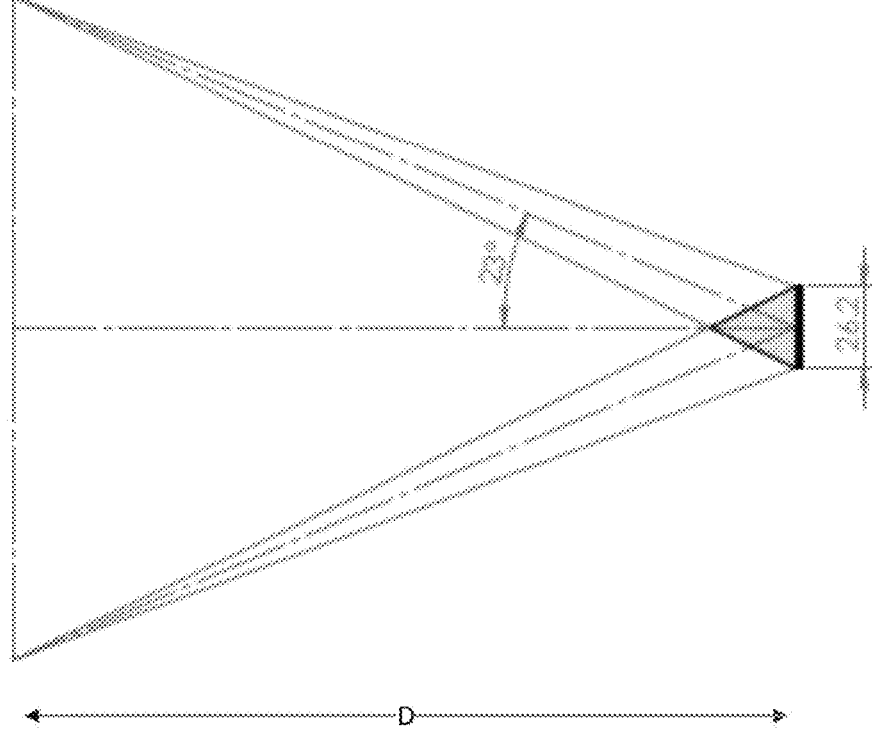
Figures 20A, 20B:
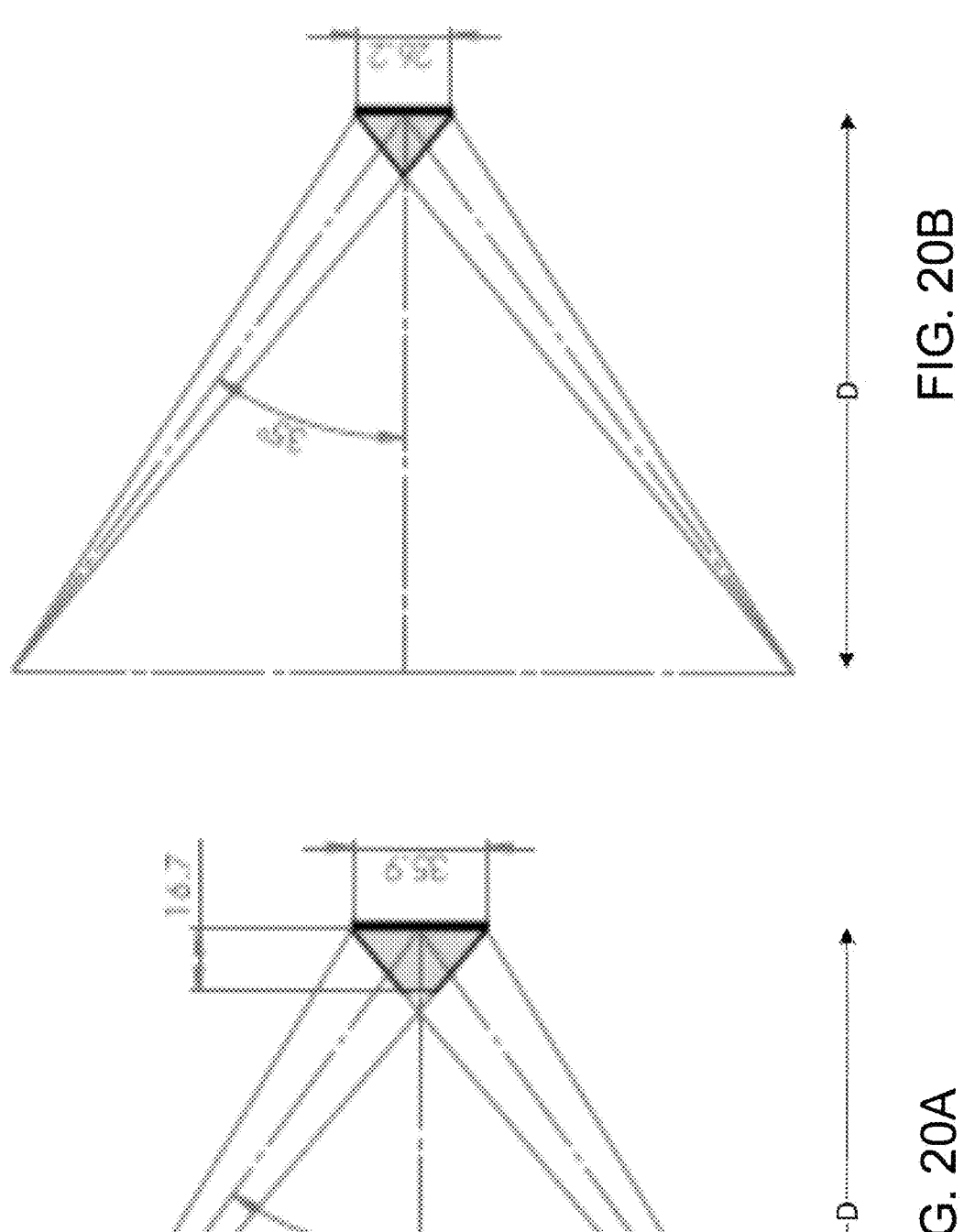
FIGS. 20A and 20B illustrate the reconstruction zone in the 3DIO system when the cone angle between the X-ray source and detector is about 35 degrees for two different sizes of detector.

Some examples of the position of the apex of the reconstruction zone for a given sensor size and given angle are illustrated in FIGS. 17-20. In FIG. 17 where the angle θ is about 15 degrees, the apex of the reconstruction zone is located about 44 mm away from a rectangular sensor having a length of about 36 mm. In FIG. 18 where the angle θ is about 20 degrees, the apex of the reconstruction zone is located about 32 mm away from a rectangular sensor having a length of about 36 mm. In FIG. 19A where the angle θ is about 23 degrees, the apex of the reconstruction zone is located about 27.5 mm away from a rectangular sensor having a length of about 36 mm. FIG. 19B illustrates a similar situation for the configuration where the rectangular sensor also has a short dimension (in this case about 26 mm) and clarifies that for the same angle (23 degrees), the location of the apex of the reconstruction zone will be determined by the shorter dimension of the two dimensions (width and length) of the rectangular sensor. This situation can be seen in the "filled-in" triangular shape rising from the face of the sensor in FIGS. 19A and 19B, where the triangular shape in FIG. 19B comes to a point whereas the triangular shape in FIG. 19A is truncated to the same height as that in FIG. 19B. In FIG. 20A where the angle θ is about 35 degrees, the apex of the reconstruction zone is located about 16.5 mm away from a rectangular sensor having a length of about 36 mm. FIG. 20B again illustrates that where the sensor is rectangular with a shorter dimension of about 26 mm, for the same angle (35 degrees), the apex of the reconstruction zone will be located about 16.5 mm away from the sensor. Thus, for a rectangular sensor, the apex of the reconstruction zone depends on the shorter dimension of the sensor. For a square sensor, though, the apex of the reconstruction zone would be the same for both dimensions.

For typical imaging of teeth, the sensor will need to be able to image regions that are as much as 1.5 cm or more away from the sensor plane in some configurations. Depending on the particular embodiment, the angle θ will need to be restricted to smaller values. In the embodiments where the imaging depth can be smaller than 17 mm, an angle θ may be about 35°. In other embodiments, the angle θ may be about 20° for an imaging depth that extends up to about 33 mm. In still other embodiments, the angle θ may be about 23° for a maximum imaging depth of about 28 mm. Still other angles may be suitable for other embodiments, depending on the image depth that is required for those applications.

Also, as can be seen from FIGS. 13-16, the distance D from the X-ray source 30 to the detector 20 may have an impact on the imaging depth or the size of the reconstruction zone, because it will affect the angular width of the X-ray beam required to fill the sensor. The distance D must meet certain minimum length requirements based on safety regulations, but the larger D becomes, the larger the over-all X-ray head will become for a given angle θ. There is also a need to ensure that D is large enough to accommodate all of the various alignments that may be required for a particular 3D imaging system. For example, if the system will need to take the equivalent of bite-wing images as well as image upper rear molars or other teeth that are located deeper into the patient's head (where other parts of the patient's anatomy such as cheek bones, shoulders, forehead, etc, may begin to interfere with placement of the X-ray head), some additional distance beyond the minimum length required by regulation may be necessary. Therefore, the distance D is most advantageously between the values of about 10 and about 35 centimeters in some embodiments to meet the existing regulations, achieve the desired images of a patient's teeth, and maintain a preferred, smaller size for the X-ray head. In other embodiments, the distance D can range between about 13 cm and about 28 cm.

In some configurations, the conical geometry of the X-ray system can be chosen to balance the factors of X-ray head size and imaging depth to arrive at an operating angle that will provide an image with a minimal blind spot yet with a sufficient reconstruction zone. Reducing the size of the X-ray head will incorporate less mass and weight and be less intimidating or bulky for the patient and the user. Reducing the X-ray head size, though, will provide a smaller cone angle and lead to a reduced Z-axis resolution and the loss of detail around any opaque objects in the teeth. At the same time, a larger cone angle will increase the Z-axis resolution of the reconstructed 3D image, but also increase the size of the X-ray head. The X-ray head size, imaging depth, and Z-axis resolution can be balanced to achieve a cone angle that will provide both a sufficient imaging depth and a reconstruction zone yielding good images of the tooth/teeth. The tooth/teeth can be located significantly over a centimeter from the sensor image plane due to the constraints of sensor size, mouth geometry, and how close to the tooth the sensor can be placed. By balancing these factors, the X-ray system be optimized for over-all image quality and utility at a cone angle of about 10 to about 35 degrees in some configurations. In other configurations, the X-ray system is optimized at a cone angle of about 15 to about 25 degrees. In other configurations, the angle can range from about 18 to about 23 degrees. In yet other configurations, the angle can range between any combination or sub-combination of these amounts.

In some embodiments of the 3DIO systems, the housing 50 can enclose the mechanical components from view, as well as being part of the mechanical structure that supports the X-ray source, motors, and other elements that enable the X-ray source 30 to rotate around axis 80. In FIGS. 5-6, unlike CBCT processes where the X-ray source horizontally rotates around the patient's head, the X-ray source 30 rotates in a circle in a plane that is roughly parallel to the X-ray detector and located on just one side of the patient's head. The detector 20 is stationary behind the tooth and in some configurations substantially parallel to the longitudinal axis of the tooth. So the X-ray source 30 can be rotated around an axis of rotation 80 that is approximately perpendicular to the plane of the detector so that the X-ray source itself rotates in a plane approximately parallel to the plane of the detector using mechanical gantry 70. As shown in FIG. 6, the X-ray source 30 is rotated around the axis of rotation 80 at a rotational velocity V that is not necessarily constant. The angle 95 shows the angular displacement between image acquisition points ("X") that are arranged evenly around the circle. There may be any number of images taken. The position of each image acquisition point is determined by dividing the circle into a number of equal segments to provide the number of images desired. Alternatively, the image acquisition points may not all be distributed equally on the circle, but a substantial portion of the total number of images desired must be distributed around a substantial portion of the circle so that a number of images are obtained at angles 95 that are significantly different for each image obtained. The X-ray source 30 does not necessarily physi- cally stop for the image acquisition, but rather is pulsed at each image acquisition point. Alternatively, the X-ray source 30 may be momentarily paused at each image acquisition point if X-ray source motion during the exposure is judged to be undesirable. The axis of rotation 80 can be centered on the detector 20 and is substantially parallel to the detector normal. But since this will be difficult to fully achieve in practice, a reconstruction algorithm can incorporate correc- tion methods to enable a quality reconstruction even with some error in the orientation of the axis of rotation 80 or other errors from the ideal reconstruction geometry. In some configurations, the axis of rotation 80 is not necessarily fixed on the center of the detector 20, but may be displaced from the center as depicted by the alternate location 85 of the axis of rotation 80. Indeed, the X-ray source 30 can rotate through any portion of the circular arc that ranges from 0 to about 360 degrees in that plane which is substantially vertical if the patient's tooth is oriented in a vertical direc- tion and the detector is aligned with the tooth. So using the 3DIO systems described herein, the operator could conceiv- ably take 2D images from any location in the parallel plane by changing the location in polar coordinates, theta and phi, rather than X and Y Cartesian coordinates. Alternatively, this same set of locations could be described using circular coordinates in the plane consisting of the radius R and the angle theta. Thus, the 3DIO system is different from some conventional tomosynthesis for mammography or chest X-rays where the source moves in a limited arc within a plane that is perpendicular to the face of the detector.

If the X-ray source moves in a uniform or substantially uniform manner (i.e., in a substantially circular motion and at a substantially constant rotational speed), its apparent instantaneous speed of movement in the X and Y directions as defined by the detector array will be sinusoidal, since it is moving in a circle. The X and Y sinusoidal movements are also 90 degrees out of phase, so that when the speed in the X direction is at a maximum, the Y movement speed is zero, and vice versa. To obtain the maximum resolution in the resulting 3D image, keeping track of where the X-ray source is in its motion and weighting the pixels appropriately for X and Y resolution during the image reconstruction must be performed. This action make sure that the images taken when the X-ray source is showing zero, or small amounts, of X-displacement are given greater value in defining the X-resolution of image features. The same approach can be performed for the Y-resolution of image features. Both of these actions will help the reconstruction algorithm reduce or eliminate motion blur caused by a continuous motion of the X-ray source during the 2D image capture process.

There exist a number of 3D reconstruction systems or methods for dental imaging known in the art. Most of these systems or approaches have failed in practice since the operator was required to manually reposition the X-ray source and take each 2D projection just as with a standard intra-oral radiograph. The substantial time required for an operator to manually take 9 to 15 intra-oral radiographs, along with the patient discomfort inherent in such a process, combined with the extended time required for 3D recon- struction process, made use of these systems or methods impractical for most dental procedures.

The 3DIO system uses an image capture process that is much quicker. This is largely due to the automated image capture that is enabled by simplifying the X-ray source motion by confining it to a circular motion in a plane that is substantially parallel to the detector and leaving the detector in the same position for each image. This method makes it possible to partially or completely automate the image capture process.

Advancements in the parallel computational power of Graphics Processing Unit (GPU) hardware have allowed clinical implementation of iterative and statistical recon- struction techniques for tomography and tomosynthesis. These iterative techniques use variational-based methods to maximize a likelihood function describing the probability of the reconstructed image given detector measurements. These advancements, when combined together with the automated capture of the 2D image data, make it practical to consider a 3DIO system as described that offers an ease of use and work flow that is comparable to standard 2D dental X-rays.

The use of these iterative techniques in the generation of the 3D image offer several advantages. First, these tech- niques are robust to missing data and arbitrary projection scans (such as scans with non-standard geometries). Second, these techniques directly model the physics and noise char- acteristics of the imaging system. And third, these tech- niques allow the use of a prior probability of the 3D reconstructed image to reduce the time required for the algorithm to converge on the correct high-resolution image.

As described herein, the systems and methods use a conical geometry in which the X-ray source(s) moves in a circular motion to take any number of 2D projection images. Each image is obtained when the X-ray source is located at a specific location in the circular motion. In some configu- rations, the circular motion can extend up to a complete circle (i.e., a full 360 degrees). In other configurations, the circular motion only extends up to part of the complete circle, for example, up to about 120, about 180, or about 270 degrees, or any degree up to 360 degrees.

As described herein, the X-ray source can move continu- ously in a circular motion as described by the conical geometry with the detector located at the apex of the cone. Some existing X-ray systems use a Carbon Nano-Tube (CNT) or Spindt-Cathode (SC) in a linear array as the X-ray source. Since the X-ray source is in a linear array configu- ration and the individual CNT or SC X-ray tube elements can be individual activated, such an array X-ray source can generate X-ray images from a variety of locations without requiring physical motion of the X-ray source. Indeed, in these systems, any motion of the X-ray source is believed to not be desirable because of concerns about vibration, com- plicated mechanics, costs, etc. But X-ray systems containing X-ray source arrays can be quite expensive because of the number of X-ray sources in the system and the increased size of the high-vacuum chamber required to contain all of them. In some configurations, the 3DIO systems do not use a linear X-ray source array and so they have a much lower cost. Instead of an array, a small X-ray source can be used to cover a large solid-angle and obtain the desired 2D projection images from a variety of locations. As well, a small X-ray source can be used to obtain the desired 2D projection images at larger angles than practical with a CNT or SC array because of the expense and difficult of building an X-ray tube vacuum chamber large enough to cover all of the desired locations and angles if an array of electron sources is used. Indeed, moving the X-ray source continuously in a circular motion provides the benefits of much lower noise and vibration than would be possible if the X-ray source motion were to stop and start for each 2D image projection. In some configurations, though, the X-ray source could rotate continuously for part of a circle, take a few images on a non-continuous basis, and then return to continuous motion.

Using a small X-ray source(s) that is rotated in a circular motion also permits a larger solid-angle sampling for the 2D image projections. This configuration provides a higher-resolution, higher-quality reconstructed image relative to configurations that use a linear X-ray source array because there is X-ray image data from a variety of locations. As depicted in FIGS. 13-16, this additional data from other viewpoints than those covered by the linear array can provide data on the structure located behind metal artifacts (such as crowns and fillings) that cannot be obtained from any location on the linear array. An X-ray source rotated in a circular motion can have a larger cone angle which will provide improved Z-axis resolution in the image as long as a sufficient number of images is obtained. And with more images obtained and a larger cone angle, it is easier to correct for image artifacts caused by opaque elements in the object (such as fillings, crowns, etc. in the tooth) because the larger number of views at broader angles provides more information about what lies behind these opaque objects in the region of interest, and shown in FIGS. 13-16. This increased information creates a more accurate and complete 3D image compared to those systems using a linear X-ray source array. This can be especially important in tomosynthesis analysis because of the limited angles and the limited number of 2D projections obtainable because of the limitations caused by an intra-oral detector, etc.

The more 2D images taken by the system, the better the resolution of the reconstructed 3D image. But the number of images that can be obtained in a reasonable amount of time can be limited both by the motion of the X-ray source and the speed with which the intra-oral X-ray sensor can capture and process images. In some embodiments, the speed is more of a limitation than the motion. In some conventional systems, dental intra-oral sensors have been operated at low speeds (i.e., 1 image frame every few seconds) because this low speed makes it easier to avoid generating heat in the sensor electronics and avoids raising the sensor temperature to a point where it would become uncomfortable in the mouth of a patient. As well, the workflow for 2D X-ray images in some conventional systems limits the acquisition rate for images to approximately 2 images per minute or less because of the time required to relocate the sensor (i.e., behind the tooth) for each image to be taken.

In some embodiments, the X-ray source must be bright enough to provide a good X-ray exposure to the detector during the small amount of time when it is pulsed on because the detector will not function properly if the dose is too low. The X-ray pulse must be short enough so that a large number of images can be obtained quickly and so that the relative motion of the X-ray source during each exposure is small. At the same time, though, the X-ray source must be relatively small in size so that the X-ray head does not become too large, and the mass of the X-ray source must be small so the mechanism moving the X-ray source in a significant part or all of a 360-degree circle in just a few seconds can be small, quiet, and light weight. Thus, in these embodiments, the voltage of the X-ray source can range from about 45 kilovolts to about 75 kilovolts, or from about 55 kilovolts to about 70 kilovolts in other embodiments. The amperage of the X-ray source can range from about 1 milliampere up to about 10 milliampere, or from about 3 milliampere to about 7 milliampere in some embodiments, with the current measured during the X-ray pulse, or when the X-ray tube is on and emitting X-rays. Again, there is a balance between involved in selecting the optimal X-ray source current for a given configuration. Since a short X-ray pulse is desired, and the detector requires a minimum X-ray exposure to function properly, it can be desirable to have a high maximum current of perhaps 10 millamperes, or perhaps even 15 milliamperes or more. However, a large maximum current will impose additional weight on the X-ray source due to larger conductors, a larger high-voltage power supply, etc., which will negatively affect other desirable aspects of the system. Therefore, a current range between about 3 milliamperes to about 7 milliamperes would be used in some embodiments.

In some configurations, the X-ray source must be designed so that it can be switched or quickly pulsed. The pulse can have a fast rise time and fall time so that the pulse provides the desired X-ray brightness and X-ray spectral characteristics for most of the pulse, again to meet the requirements for sensor X-ray exposure and for 3D reconstructed image quality. In these configurations, a gated cathode-type X-ray tube can be used because pulsing the X-ray source power supply cannot meet these pulse characteristics as easily or as well. It has been found that a rise time of about 1 millisecond and a fall time of about 1 millisecond can be achieved fairly easily with the gated cathode-type X-ray tube. With some effort these values could be further reduced to about 0.5 millisecond or even shorter, such as even 0.25 milliseconds. Given that the desired X-ray pulse is about 10 millseconds to about 40 milliseconds in length, it would be desirable that the rise time and fall time be less than about 20% of the pulse length. For a pulse length of about 40 milliseconds, this would imply a maximum rise time and fall time of about 8 milliseconds. Other X-ray tube structures that can be used in place of, or in combination with, the gated cathode-type X-ray tube include Carbon NanoTubes (CNT), Spindt Cathodes, micro-machined structures as electron emitters, and/or heated Tungsten-filament cathodes.

In some embodiments, the X-ray detector should also meet specific requirements. A first requirement is that sensor image acquisition rate or frame rate must be high enough to capture a sufficient number of images to produce a good reconstructed image. In some configurations, the sensor image acquisition rate can range from about 5 to about 25 images/second. In other configurations, the sensor image acquisition rate can range from about 10 to about 15 images/second. A second requirement is that it should limit the over-all image acquisition time to a few seconds for reasons of patient comfort and reducing the concern about patient inadvertent motion that could disturb or disrupt the imaging process. A third requirement is that the detector should be able to provide a resolution that is on the order of the state of the art for 2D intra-oral X-ray, or a pixel size that ranges from about 15 μm to about 30 μm square.

The 3DIO systems described herein exhibit several helpful features. One helpful feature of the 3DIO systems includes the ability to obtain high resolution 3D images while employing X-ray dose minimization schemes. Prior to the 3DIO systems described herein, to obtain a 3D image with a resolution of 100 microns or better typically required X-ray dosages ranging from 300 µSv to 1,000 µSv. The 3DIO systems described herein allow the operator to get a similar resolution with much smaller dosages ranging from about 10 µGray up to about 55 µGray.

Another helpful feature includes the increased imaging efficacy. This efficacy can be achieved since the system interfaces and synchronizes low-power X-ray tubes with CMOS sensors and collects 2D images from multiple angles, thereby reducing the number of images needed to achieve diagnostic quality images by optimizing the spatial resolution, noise, contrast-to-noise ratio, and geometric accuracy. This will provide benefits to the practicing dentist by providing better diagnostic images of teeth with cracks, interproximal caries, overlapping roots (when viewed in 2D radiographs), and other anomalous anatomy and diagnostic challenges in dentistry.

The 3DIO systems described herein can perform comparably to tuned aperture computed tomography (TACT) systems more rapidly and at lower cost. TACT systems employ dental tomosynthesis with intra-oral sensors that can be more accurate than CBCT in detecting some tooth fractures. Indeed, commercial software for the 3D reconstruction of tomosynthesis data using TACT has been developed. Unfortunately, this approach failed in clinical practice, primarily because the operator was required to manually reposition the X-ray source and take each 2D image similar to a standard intra-oral radiograph. This illustrates the importance and value of the 3DIO imaging approach which avoids the requirement that the X-ray source be manually repositioned.

An attractive feature of the 3DIO systems described herein is its adaptability for a dental practice. Dental imaging must meet a number of constraints to be adopted into a dental practice in addition to just providing a reduced X-ray dosage and improved resolution over the existing CBCT approaches. CBCT procedures, and some conventional 3D dental imaging systems and approaches, have not been successful in achieving broad acceptance into standard dental practice because they impose unacceptable burdens on the patient and on the practice of dentistry. These burdens include issues of unacceptable monetary cost; unacceptable or unattractive burdens born by the patient such as personal discomfort, X-ray dose, and time at the dentist to receive treatment; and disruption of the work flow in the dental practice. Each of these issues needs to be addressed and resolved in order to create a 3D dental imaging system that will be of interest to the majority of dental practices.

By way of explanation, a typical work flow in a dental practice for taking 2D images of a tooth is as follows. The dental technician or dentist will insert a digital imaging detector into the patient's mouth that is sized to fit with some level of comfort into the mouth. The X-ray source is then positioned external to the patient's mouth with the radiation from the X-ray source aimed at the detector appropriately, and then the X-ray source is triggered and a single image is obtained. The entire process to obtain a single X-ray image typically takes 30-60 seconds, with additional images requiring less additional time because the required equipment is already in the approximately correct position.

To achieve a similar work-flow for a 3D dental image, several requirements should be met. The first requirement is that the X-ray source must be low weight and relatively small so that it may be mounted on the wall or on a small and mobile cart similar to standard dental X-ray equipment and readily and easily positioned as necessary. Alternatively, it may be mounted in other ways that provide for the appropriate positioning. The second requirement is that the intra-oral detector must be similar in size, feel, patient comfort level, etc. to existing intra-oral detectors. The third requirement is that the entire imaging process must be able to be completed within a relatively short period of time, such as 5 to 10 seconds. The fourth requirement is that positioning of the X-ray source with respect to the patient and the intraoral detector be easily and quickly accomplished.

As well, a typical 2D dental image is obtained without any constraints on the patient's movement or position other than a verbal request to remain motionless while the image is taken. A 3D dental imaging process that imposes significant discomfort on the patient by imposing a head restraining device or by requiring that a large X-ray source device be positioned next to the patient's head would cause significant patient discomfort and consequent patient resistance to the use of 3D imaging as standard practice.

Meeting the need for a similar level of patient comfort imposes the following constraints on the 3D dental imaging systems. First, in order to avoid any kind of head motion restraint that would be more uncomfortable than a simple chin rest or similar approach, the 3D imaging process must be accomplished quickly, on the order of less than 5 seconds, and certainly less than 10 seconds. Since the number of 2D images required for an accurate 3D rendering is typically between about 15 images and 50 images, the 2D image capture rate needs to be at least on the order of 5 or more images per second. In other embodiments, the number of 2D images required for an accurate 3D rendering can range up to 75 or even 100 images, so the 2D image capture rate needs to be at least on the order of about 7.5 or even 10 or more images per second.

The second constraint is that the X-ray source needs to be small and appear to be similar in size and shape to existing X-ray sources with which patients are familiar. And since the imaging process must be completed quickly, and the X-ray source must move in an arc, circle, or some other geometric path in order to obtain the required 2D images, the X-ray source should be light weight in order to simplify the issues of managing the required mechanical motion, counter-weights, and other engineering concerns, and also physically small. It is desirable that the X-ray source itself weigh less than about 1.3 Kg, or about 1.5 Kg, and certainly less than about 5 Kg, and that it be less than about 13 cm in length, about 7 cm in width, and about 8 cm in height.

A third constraint concerns the speed and capability of the computer processor that performs the mathematically complex calculations required to reconstruct a 3D image. It is helpful that the 3D calculations be completed within a short time after the 2D image data is gathered, again in order to meet the requirements on patient comfort and acceptance, and to fit within the workflow of the typical dental practice. It is expected that the time required to present the 3D data to the dentist should not be more than about 90 seconds.

Finally, meeting the challenge of monetary cost imposes constraints on the technology that can be implemented in the 3D imaging system. Some approaches use an X-ray source array for 3D dental imaging, but this imposes significant costs because it does not take advantage of the existing, inexpensive, well developed, reliable vacuum tube X-ray sources that are currently available. Utilizing an advanced X-ray source array, while being technically attractive, offers little advantage to the dental practitioner or to the dental patient in terms of image quality, X-ray dose, or other important performance factors over the lower-cost conventional X-ray source that can easily be moved and pulsed rapidly to generate the required 2D X-ray images within the desired time limitations.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for making a three dimensional image of an object, comprising:

providing an X-ray source on a first side of an object to be imaged;

positioning a substantially stationary X-ray detector on an opposite side of the object from the X-ray source;

moving the X-ray source in a circular motion to multiple positions on the first side of the object;

collecting multiple two dimensional (2D) images of the object in less than about 10 seconds when the X-ray source is located in the multiple positions;

wherein the process for moving the X-ray source and collecting the multiple 2D images can range from about 15 ms to about 140 ms per image taken; and reconstructing a three-dimensional (3D) image using the multiple 2D images.

2. The method of claim 1, further comprising collecting 50 to 100 2D images.

3. The method of claim 1, further comprising collecting the multiple 2D images of the object in less than about 5 seconds.

4. The method of claim 3, further comprising collecting 15 to 50 2D images.

5. The method of claim 1, further comprising collecting the multiple 2D images of the object in less than about 3 seconds.

6. The method of claim 1, further comprising pulsing the X-ray source for about 5 ms to about 40 ms per image in each of the multiple positions.

7. The method of claim 6, further comprising pulsing the X-ray source for about 10 ms to about 30 ms per image.

8. The method of claim 1, wherein the process for moving the X-ray source and collecting the multiple 2D images can range from about 30 ms to about 45 ms per image taken.

9. The method of claim 1, wherein the object comprises a tooth.

10. A method for making a three dimensional image of an object, comprising:

providing an X-ray source on a first side of an object to be imaged;

positioning a substantially stationary X-ray detector on an opposite side of the object from the X-ray source;

moving the X-ray source in a circular motion to multiple positions on the first side of the object;

collecting 15 to 100 two dimensional (2D) images of the object by pulsing the X-ray source for about 5 ms to about 40 ms per image in each of the multiple positions;

wherein the process for moving the X-ray source and collecting the 2D images can range from about 15 ms to about 140 ms per image taken; and reconstructing a three-dimensional (3D) image using the multiple 2D images.

11. The method of claim 10, further comprising pulsing the X-ray source for about 10 ms to about 30 ms per image.

12. The method of claim 10, further comprising collecting 30 to 75 2D images.

13. The method of claim 10, further comprising collecting the 2D images in less than about 10 seconds.

14. The method of claim 10, further comprising collecting the 2D images in less than about 5 seconds.

15. The method of claim 10, further comprising collecting the multiple 2D images of the object in less than about 3 seconds.

16. The method of claim 10, wherein the process for moving the X-ray source and collecting the multiple 2D images can range from about 30 ms to about 45 ms per image taken.

17. The method of claim 10, wherein the object comprises a tooth.

18. A method for making a three dimensional image of a tooth, comprising:

providing an X-ray source on a first side of an object to be imaged;

positioning a substantially stationary X-ray detector on an opposite side of the object from the X-ray source;

moving the X-ray source in a circular motion to multiple positions on the first side of the object;

collecting 15 to 100 two dimensional (2D) images of the object in less than about 10 seconds while pulsing the X-ray source for about 5 ms to about 40 ms per image when the X-ray source is located in the multiple positions;

wherein the process for moving the X-ray source and collecting the 2D images can range from about 15 ms to about 140 ms per image taken; and reconstructing a three-dimensional (3D) image using the multiple 2D images.

19. The method of claim 18, further comprising collecting the multiple 2D images of the object in less than about 10 seconds.

20. The method of claim 18, wherein the object comprises a tooth.

* * * * *